United States Patent
Rotem et al.

(10) Patent No.: US 11,047,003 B2
(45) Date of Patent: Jun. 29, 2021

(54) SYSTEMS AND METHODS FOR EPIGENETIC SEQUENCING

(71) Applicants: President and Fellows of Harvard College, Cambridge, MA (US); The General Hospital Corporation, Boston, MA (US)

(72) Inventors: Assaf Rotem, Cambridge, MA (US); Oren Ram, Chestnut Hill, MA (US); Bradley E. Bernstein, Cambridge, MA (US); David A. Weitz, Cambridge, MA (US)

(73) Assignees: The General Hospital Corporation, Boston, MA (US); President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 15/670,929

(22) Filed: Aug. 7, 2017

(65) Prior Publication Data

US 2018/0023133 A1 Jan. 25, 2018

Related U.S. Application Data

(63) Continuation of application No. 14/478,672, filed on Sep. 5, 2014, which is a continuation-in-part of application No. PCT/US2013/029123, filed on Mar. 5, 2013.

(60) Provisional application No. 61/634,744, filed on Mar. 5, 2012.

(51) Int. Cl.
| | | |
|---|---|---|
| *C12Q 1/6869* | (2018.01) | |
| *B01F 13/00* | (2006.01) | |
| *B01L 3/00* | (2006.01) | |

(52) U.S. Cl.
CPC ........ *C12Q 1/6869* (2013.01); *B01F 13/0071* (2013.01); *B01L 3/502784* (2013.01)

(58) Field of Classification Search
CPC ........ C12Q 1/68; C12Q 1/6869; C07H 21/00; B01F 13/0071; B01L 3/502784
See application file for complete search history.

(56) References Cited

U.S. PATENT DOCUMENTS

| | | |
|---|---|---|
| 5,750,346 A | 5/1998 | Andre et al. |
| 6,013,445 A | 1/2000 | Albrecht et al. |
| 6,054,278 A | 4/2000 | Dodge et al. |
| 6,312,911 B1 | 11/2001 | Bancroft et al. |
| 6,696,022 B1 | 2/2004 | Chen et al. |
| 6,750,016 B2 | 6/2004 | Mirkin et al. |
| 6,974,669 B2 | 12/2005 | Mirkin et al. |
| 7,708,949 B2 | 5/2010 | Stone et al. |
| 8,293,535 B2 | 10/2012 | Farquar et al. |
| 8,337,778 B2 | 12/2012 | Stone et al. |
| 8,592,150 B2 | 11/2013 | Drmanac et al. |
| 8,765,485 B2 | 7/2014 | Link et al. |
| 8,778,609 B1 | 7/2014 | Umbarger |
| 8,829,171 B2 | 9/2014 | Steemers et al. |
| 8,841,071 B2 | 9/2014 | Link |
| 9,023,650 B2 | 5/2015 | Farquar et al. |
| 9,388,465 B2 | 7/2016 | Hindson et al. |
| 9,410,201 B2 | 8/2016 | Hindson et al. |
| 9,567,631 B2 | 2/2017 | Hindson et al. |
| 9,644,204 B2 | 5/2017 | Hindson et al. |
| 9,689,024 B2 | 6/2017 | Hindson et al. |
| 9,694,361 B2 | 7/2017 | Bharadwaj et al. |
| 9,695,468 B2 | 7/2017 | Hindson et al. |
| 9,701,998 B2 | 7/2017 | Hindson et al. |
| 9,708,654 B2 | 7/2017 | Hunicke-Smith et al. |
| 10,596,541 B2 | 3/2020 | Weitz et al. |
| 2002/0026046 A1 | 2/2002 | Pasloske et al. |
| 2003/0082668 A1* | 5/2003 | Tamai .................. C12Q 1/34 435/24 |
| 2003/0152994 A1 | 8/2003 | Woudenberg et al. |

(Continued)

FOREIGN PATENT DOCUMENTS

| | | |
|---|---|---|
| CN | 101946010 A1 | 1/2011 |
| CN | 102439177 A | 5/2012 |

(Continued)

OTHER PUBLICATIONS

Li et al., The Sequence Alignment/Map format and SAMtools Bioinformatics 25 (16) : 2078-2079 (Year: 2009).*
Meyer et al., Targeted high-throughput sequencing of tagged nucleic acid samples. Nucleic Acids Research 35(15) : e97 (Year: 2007).*
Meyer et al., Illumina Sequencing Library Preparation for Highly Multiplexed Target Capture and Sequencing. Cold Spring Harbor Protoc; 2010; doi:10.1101/pdb.prot5448 (Year: 2010).*

(Continued)

*Primary Examiner* — Ethan C Whisenant
(74) *Attorney, Agent, or Firm* — Wolf, Greenfield & Sacks, P.C.

(57) ABSTRACT

The present invention generally relates to microfluidics and/or epigenetic sequencing. In one set of embodiments, cells contained within a plurality of microfluidic droplets are lysed and the DNA (e.g., from nucleosomes) within the droplets are labeled, e.g., with adapters containing an identification sequence. The adapters may also contain other sequences, e.g., restriction sites, primer sites, etc., to assist with later analysis. After labeling with adapters, the DNA from the different cells may be combined and analyzed, e.g., to determine epigenetic information about the cells. For example, the DNA may be separated on the basis of certain modifications (e.g., methylation), and the DNA from the separated nucleosomes may be sequenced using techniques such as chromatin immunoprecipitation ("ChIP"). In some cases, the DNA sequences may also be aligned with genomes, e.g., to determine which portions of the genome were epigenetically modified, e.g., via methylation.

14 Claims, 15 Drawing Sheets

Specification includes a Sequence Listing.

(56) References Cited

U.S. PATENT DOCUMENTS

| | | | |
|---|---|---|---|
| 2005/0266407 A1* | 12/2005 | Chee | C07H 21/00 435/6.11 |
| 2006/0137434 A1 | 6/2006 | Cohen et al. | |
| 2006/0153924 A1 | 7/2006 | Griffiths et al. | |
| 2007/0000342 A1 | 1/2007 | Link et al. | |
| 2007/0031865 A1* | 2/2007 | Willoughby | C12N 15/1093 435/6.1 |
| 2007/0052781 A1 | 3/2007 | Fraden et al. | |
| 2007/0077572 A1 | 4/2007 | Tawfik et al. | |
| 2007/0195127 A1 | 8/2007 | Ahn et al. | |
| 2008/0268450 A1 | 10/2008 | Nam et al. | |
| 2009/0098555 A1 | 4/2009 | Roth et al. | |
| 2009/0105959 A1 | 4/2009 | Braverman et al. | |
| 2009/0181375 A1 | 7/2009 | Peter et al. | |
| 2009/0181864 A1 | 7/2009 | Chai et al. | |
| 2009/0203063 A1 | 8/2009 | Wheeler et al. | |
| 2009/0208975 A1 | 8/2009 | D'Costa et al. | |
| 2010/0022414 A1 | 1/2010 | Link et al. | |
| 2010/0105052 A1 | 4/2010 | Drmanac et al. | |
| 2010/0120097 A1 | 5/2010 | Aglyamova et al. | |
| 2010/0136544 A1 | 6/2010 | Agresti et al. | |
| 2010/0216151 A1* | 8/2010 | Lapidus | C12Q 1/6883 435/6.1 |
| 2010/0248237 A1 | 9/2010 | Froehlich et al. | |
| 2010/0261230 A1 | 10/2010 | Liu et al. | |
| 2010/0285975 A1 | 11/2010 | Mathies et al. | |
| 2010/0323361 A1 | 12/2010 | Pugh et al. | |
| 2011/0033854 A1 | 2/2011 | Drmanac et al. | |
| 2011/0267457 A1 | 11/2011 | Agresti et al. | |
| 2011/0275063 A1 | 11/2011 | Weitz et al. | |
| 2011/0281736 A1 | 11/2011 | Drmanac et al. | |
| 2011/0318786 A1 | 12/2011 | Reichert et al. | |
| 2012/0010091 A1 | 1/2012 | Linnarson | |
| 2012/0015822 A1 | 1/2012 | Weitz et al. | |
| 2012/0028818 A1 | 2/2012 | Öhman et al. | |
| 2012/0058468 A1 | 3/2012 | Mckeown | |
| 2012/0122714 A1 | 5/2012 | Samuels et al. | |
| 2012/0132288 A1 | 5/2012 | Weitz et al. | |
| 2012/0157322 A1* | 6/2012 | Myllykangas | C12Q 1/6837 506/2 |
| 2012/0022094 A1 | 8/2012 | Samuels et al. | |
| 2012/0196758 A1 | 8/2012 | Klausing et al. | |
| 2012/0211084 A1 | 8/2012 | Weitz et al. | |
| 2012/0220494 A1 | 8/2012 | Samuels et al. | |
| 2012/0309002 A1 | 12/2012 | Link et al. | |
| 2012/0322691 A1* | 12/2012 | Sachidanandam | C12Q 1/6855 506/16 |
| 2013/0005585 A1 | 1/2013 | Anderson et al. | |
| 2013/0130919 A1 | 5/2013 | Chen et al. | |
| 2013/0165346 A1 | 6/2013 | Wang et al. | |
| 2013/0178369 A1 | 7/2013 | Burns et al. | |
| 2013/0219534 A1 | 8/2013 | Wong et al. | |
| 2013/0225418 A1 | 8/2013 | Watson | |
| 2013/0261019 A1 | 10/2013 | Lin et al. | |
| 2013/0261027 A1 | 10/2013 | Li et al. | |
| 2013/0274117 A1 | 10/2013 | Church et al. | |
| 2014/0057799 A1 | 2/2014 | Johnson et al. | |
| 2014/0141436 A1 | 5/2014 | Erlich et al. | |
| 2014/0194324 A1 | 7/2014 | Gormley et al. | |
| 2014/0200162 A1 | 7/2014 | Saito et al. | |
| 2014/0228255 A1 | 8/2014 | Hindson et al. | |
| 2014/0274729 A1 | 9/2014 | Kurn et al. | |
| 2014/0378345 A1 | 12/2014 | Hindson et al. | |
| 2015/0011432 A1 | 1/2015 | Saxonov | |
| 2015/0034163 A1 | 2/2015 | Abate et al. | |
| 2015/0051117 A1 | 2/2015 | Church et al. | |
| 2015/0057163 A1 | 2/2015 | Rotem et al. | |
| 2015/0298091 A1 | 10/2015 | Weitz et al. | |
| 2015/0329852 A1 | 11/2015 | Nolan | |
| 2015/0344938 A1 | 12/2015 | Andersen et al. | |
| 2016/0145683 A1 | 5/2016 | Fan et al. | |
| 2016/0194694 A1 | 7/2016 | Andersen et al. | |
| 2016/0312213 A1 | 10/2016 | Rokhsar et al. | |
| 2017/0028377 A1 | 2/2017 | Bernstein et al. | |
| 2017/0029813 A1 | 2/2017 | Weitz et al. | |
| 2018/0071705 A1 | 3/2018 | Weitz et al. | |
| 2018/0087078 A1 | 3/2018 | Weitz et al. | |
| 2018/0155777 A1 | 6/2018 | Weitz et al. | |
| 2018/0155778 A1 | 6/2018 | Weitz et al. | |
| 2018/0265922 A1 | 9/2018 | Weitz et al. | |
| 2018/0304222 A1 | 10/2018 | Weitz et al. | |
| 2018/0371540 A1 | 12/2018 | Hindson et al. | |
| 2019/0361010 A1 | 11/2019 | Belhocine et al. | |
| 2020/0123582 A1 | 4/2020 | Tan et al. | |

FOREIGN PATENT DOCUMENTS

| | | |
|---|---|---|
| CN | 103717749 A | 4/2014 |
| EP | 2 359 689 A1 | 8/2011 |
| JP | 2007-503984 A | 3/2007 |
| JP | 2010-520749 A | 6/2010 |
| JP | 2010-193884 A | 9/2010 |
| JP | 2011-509075 | 3/2011 |
| JP | 2014-512826 A | 5/2014 |
| JP | 2015-528283 A | 9/2015 |
| JP | 2017-515469 A | 6/2017 |
| WO | WO 2004/002627 A2 | 1/2004 |
| WO | WO 2004/091763 A2 | 10/2004 |
| WO | WO 2005/021151 A1 | 3/2005 |
| WO | WO 2005/062982 A2 | 7/2005 |
| WO | WO 2006/096571 A2 | 9/2006 |
| WO | WO 2007/089541 A2 | 8/2007 |
| WO | WO 2008/000090 A1 | 1/2008 |
| WO | WO 2008/109176 A2 | 9/2008 |
| WO | WO 2008/127789 A2 | 10/2008 |
| WO | WO 2009/011808 A1 | 1/2009 |
| WO | WO 2009/085215 A1 | 7/2009 |
| WO | WO 2010/025310 A2 | 3/2010 |
| WO | WO 2010/033200 A2 | 3/2010 |
| WO | WO 2010/080134 A1 | 7/2010 |
| WO | WO 2010/151776 A2 | 12/2010 |
| WO | WO 2011/056546 A1 | 5/2011 |
| WO | WO 2011/140510 A2 | 11/2011 |
| WO | WO 2012/003330 A2 | 1/2012 |
| WO | WO 2012/016136 A2 | 2/2012 |
| WO | WO 2012/019765 A1 | 2/2012 |
| WO | WO 2012/048340 A2 | 4/2012 |
| WO | WO 2012/048341 A1 | 4/2012 |
| WO | WO 2012/083225 A2 | 6/2012 |
| WO | WO 2012/094642 A2 | 7/2012 |
| WO | WO 2012/112804 A1 | 8/2012 |
| WO | WO 2012/128717 A1 | 9/2012 |
| WO | WO 2012/149042 A2 | 11/2012 |
| WO | WO 2012/162267 A2 | 11/2012 |
| WO | WO 2013/011611 A1 | 1/2013 |
| WO | WO 2013/116698 A2 | 8/2013 |
| WO | WO 2013/123125 A1 | 8/2013 |
| WO | WO 2013/134261 A1 | 9/2013 |
| WO | WO 2013/188872 A1 | 12/2013 |
| WO | WO 2014/028537 A | 2/2014 |
| WO | WO 2014/047561 A1 | 3/2014 |
| WO | WO 2014/145555 A1 | 9/2014 |
| WO | WO 2014/210353 A2 | 12/2014 |
| WO | WO 2015/103339 A1 | 7/2015 |
| WO | WO 2015/160919 A1 | 10/2015 |
| WO | WO 2015/161177 A1 | 10/2015 |
| WO | WO 2015/164212 A1 | 10/2015 |
| WO | WO 2015/200541 A1 | 12/2015 |
| WO | WO 2016/040476 A1 | 3/2016 |
| WO | WO 2016/168584 A1 | 10/2016 |

OTHER PUBLICATIONS

Nielsen et al., DeepSAGE—digital transcriptomics with high sensitivity, simple experimental protocol and multiplexing of samples. Nucleic Acids Research 34(19) :e133 (Year: 2006).*

Saha et al., Using the tanscriptome to annotate the genome. Nature Biotechnology 19 :508 (Year: 2002).*

Velculescu et al., Serial Analysis of Gene Expression. Science 270 : 484 (Year: 1995).*

(56) References Cited

OTHER PUBLICATIONS

Zheng et al., Titration-free massively parallel pyrosequencing using trace amounts of starting material. Nucleic Acids Research 38(13) : e137 (Year: 2010).*

Buermans et al., New methods for next generation sequencing based microRNA expression profiling. BMC Genomics 11 :716 (Year: 2010).*

Craig et al., Identification of genetic variants using bar-coded multiplexed sequencing. Nature Methods 5(10) : 887 (Year: 2008).*

Islam et al., Characterization of the single-cell transcriptional landscape by highly multiplex RNA-seq. Genome Research 21 :1160 (Year: 2011).*

Kato, K., RNA fingerprinting by molecular indexing. Nucleic Acids Research 24(2) : 394 (Year: 1996).*

Lau et al.,An Abundant Class of Tiny RNAs with Probable Regulatoryr roles in Caenorhabditis elegans. Science 294 :858 (Year: 2001).*

Moreau et al., Chronological Changes in MicroRNA Expression in the Developing Human Brain. Plos One 8(4) : e60480 (Year: 2013).*

Nieuwerburgh et al., Quantitative Bias in Illumina TruSeq and a Novel Post Amplification Barcoding Strategy for Multiplexed DNA and Small RNA Deep Sequencing. Plos One 6(10) : e26969 (Year: 2011).*

Ross et al.Reverse Transcription with Random Pentadecamer Primers Improves the Detection Limit of a Quantitative PCR Assay for BCR-ABL Transcripts in Chronic Myeloid Leukemia : Implications for defining sensitivity in Minimal Residual Disease. Clinical Chemistry 54 (9) : 1568 (Year: 2008).*

Shi et al., Poly(T) Adaptor RT-PCR. Ch. 4 in Methods in Molecular Biology p. 53(Ed by Jian-Bing Fan. (Year: 2012).*

Vigneault et al., Efficient microRNA capture and bar-coding via enzymatic oligonucleotide adenylation. Nature Methods 5(9) : 777 (Year: 2008).*

Chinese Office Action dated Jun. 5, 2020 for Application No. 201580029045.4.

Chinese Office Action dated Jun. 23, 2020 for Application No. 201580029081.0.

European Office Action dated Mar. 10, 2020 for Application No. EP18201501.6.

Japanese Office Action dated Aug. 4, 2020 for Application No. JP 2016-564093.

Chinese Office Action dated Apr. 26, 2020 for Application No. CN 201680031721.6.

Japanese Office Action dated Mar. 31, 2020 for Application No. 2017-554339.

Final Office Action dated Jul. 22, 2020 for U.S. Appl. No. 15/303,874.

Office Action dated Feb. 20, 2020 for U.S. Appl. No. 15/303,893.

Office Action dated Feb. 4, 2020 for U.S. Appl. No. 14/734,903.

Office Action dated Jun. 1, 2020 for U.S. Appl. No. 15/991,600.

Office Action dated Mar. 19, 2020 for U.S. Appl. No. 15/836,520.

Office Action dated Jul. 17, 2020 for U.S. Appl. No. 15/965,452.

Office Action dated Apr. 21, 2020 for U.S. Appl. No. 15/566,904.

Cheng et al., Anisotropic colloidal crystal particles from microfluidics. J Colloid Interface Sci. 2014;421:64-70.

Lu et al., Construction of small RNA cDNA libraries for deep sequencing. Methods. 2007;43(2):110-117.

Meyer et al., Parallel tagged sequencing on the 454 platform. Nat Protoc. 2008;3(2):267-278.

Rothberg et al., The development and impact of 454 sequencing. Nat Biotechnol. 2008;26(10):1117-1124.

Office Action dated Nov. 5, 2020 for U.S. Appl. No. 15/836,520.

Guo et al., Resolution of cell fate decisions revealed by single-cell gene expression analysis from zygote to blastocyst. Dev Cell. Apr. 20, 2010;18(4):675-85.

Tang et al., mRNA-Seq whole-transcriptome analysis of a single cell. Nat Methods. May 2009;6(5):377-82.

Extended European Search Report for EP 13758373.8 dated Nov. 24, 2015.

European Office Action dated Nov. 18, 2016 for Application No. EP 13758373.8.

International Search Report and Written Opinion dated May 23, 2013 for Application No. PCT/US2013/029123.

International Preliminary Report on Patentability dated Sep. 18, 2014 for Application No. PCT/US2013/029123.

International Search Report and Written Opinion for PCT/US2015/026338 dated Sep. 8, 2015.

International Preliminary Report on Patentability dated Oct. 27, 2016 for Application No. PCT/US2015/026338.

International Search Report and Written Opinion for PCT/US2015/026422 dated Sep. 2, 2015.

International Preliminary Report on Patentability dated Oct. 27, 2016 for Application No. PCT/US2015/026422.

International Search Report and Written Opinion for PCT/US2015/026443, dated Jul. 27, 2015.

International Preliminary Report on Patentability dated Nov. 3, 2016 for Application No. PCT/US2015/026443.

International Search Report and Written Opinion for PCT/US2016/027734 dated Jul. 14, 2016.

[No Author Listed] Single-Cell Whole Transcriptome Profiling With the SOLiD System. AB Applied Biosystems. Apr. 2009 Publication 139AP16-01: 6 pages.

Barbazuk et al., SNP discovery via 454 transcriptome sequencing. Plant J. Sep. 2007;51(5):910-8. Epub Jul. 27, 2007.

Binladen et al., The use of coded PCR primers enables high-throughput sequencing of multiple homolog amplification products by 454 parallel sequencing. PLoS One. Feb. 14, 2007;2(2):e197.*

Brouzes et al., Droplet microfluidic technology for single-cell high-throughput screening. Proc Natl Acad Sci U S A. Aug. 25, 2009;106(34):14195-200. doi: 10.1073/pnas.0903542106. Epub Jul. 15, 2009.

Dutchen, Beyond average. Harvard Medical School News. May 21, 2015. Accessed online May 28, 2015 at http://hms.harvard.edu/news/beyond-average. 6 pages.

Fan et al., Expression profiling. Combinatorial labeling of single cells for gene expression cytometry. Science. Feb. 6, 2015;347(6222): 1258367. doi: 10. 1 126/science.1258367.

Guo et al., Droplet microfluidics for high-throughput biological assays. Lab Chip. Jun. 21, 2012;12(12):2146-55. doi: 10.1039/c21c21147e. Epub Feb. 9, 2012.

Hamady et al., Error-correcting barcoded primers for pyrosequencing hundreds of samples in multiplex. Nat Methods. Mar. 2008;5(3):235-7.

Heuze et al., Molecular analysis of a pro-T cell clone transformed by Abelson-murine leukemia virus, displaying progressive gamma delta T cell receptor gene rearrangement and surface expression. Eur J Immunol. Aug. 1992;22(8):2077-84.

Hug et al., A chromatin immunoprecipitation screen reveals protein kinase Cbeta as a direct RUNX1 target gene. J Biol Chem. Jan. 9, 2004,279(2):825-30. Epub Oct. 15, 2003.

Jaitin et al., Massively parallel single-cell RNA-seq for marker-free decomposition of tissues into cell types. Science. Feb. 14, 2014;343(6172):776-9. doi: 10.1 126/science.1247651.

Karow, Harvard groups develop fast, inexpensive droplet methods for RNA-seq of thousands of single cells. GenomeWeb. May 21, 2015. Accessed online May 27, 2015 at https ://www. genome web .com/sequencing-technology /harvard-groups-develop-fast-inexpensivedroplet-methods-rna-seq-thousands. 4 pages.

Klein et al., Droplet harcoding for single-cell transcriptomics applied to embryonic stem cells. Cell. May 21, 2015;161(5):1187-201. doi:10.1016/j.cel1.2015.04.044.

Koster et al., Drop-based microfluidic devices for encapsulation of single cells. Lab Chip. 2008; 8:1110-1115.

Kumaresan et al., High-Throughput Single Copy DNA Amplification and Cell Analysis in Engineered Nanoliter Droplets. Anal Chem. May 15, 2008;80(10):3522-9.

Li et al., Sequence-specific label-free DNA sensors based on silicon nanowires. Nano Lett Feb. 4, 2004(2): 245-7.

Macosko et al., Highly parallel genome-wide expression profiling of individual cells using nanoliter droplets. Cell. May 2015;161:1202-1214.

Margulies et al., Genome sequencing in microfabricated high-density picolitre reactors. Nature. Sep. 15, 2005;437(7057):376-80. Epub Jul. 31, 2005.

(56) References Cited

OTHER PUBLICATIONS

Meyer et al., Targeted high-throughput sequencing of tagged nucleic acid samples. Nucleic Acids Res. ePub Aug. 1, 2007; 35(15):e97,1-5.
Ng et al., Multiplex sequencing of paired-end ditags (MS-PET): a strategy for the ultra-high-throughput analysis of transcriptomes and genomes. Nucleic Acids Res. Jul. 13, 2006;34(12):e84.
Nielsen et al., DeepSAGE—digital transcriptomics with high sensitivity, simple experimental protocol and multiplexing of samples. Nucleic Acids Res. 2006;34(19):e133. Epub Oct. 5, 2006.
Novak et al., Single-cell multiplex gene detection and sequencing with microfluidically generated agarose emulsions. Angew Chem Int Ed Engl. Jan. 10, 2011;50(2):390-5. doi: 10.1002/anie.201006089.
Rotem et al., High-Throughput Single-Cell Labeling (Hi-SCL) for RNA-Seq Using Drop-Based Microfluidics. PLoS One. May 22, 2015;10(5):e0116328. doi:10.1371/journal.pone.0116328. eCollection 2015.
Schones et al., Dynamic regulation of nucleosome positioning in the human genome. Cell. Mar. 7, 2008; 132(5):887-898.
Sokoloff, Effects of Capillary Forces on a Hydrogel Sphere Pressed against a Surface. Langmuir. Jan. 12, 2016;32(1):135-9. doi: 10.1021/acs.langmuir.5b04012. Epub Dec. 24, 2015.
Tewhey et al., Microdroplet-based PCR enrichment for large-scale targeted sequencing. Nat Biotechnol. Nov. 2009;27(11):1025-31. doi: 10.1038/nbt.1583.
Wang et al., Novel thermosensitive hydrogel injection inhibits post-infarct ventricle remodelling. Eur J Heart Fail. Jan. 2009;11(1):14-19. doi: 10.1093/eurjhf/hfn009.
Weber et al., Chromosome-wide and promoter-specific analyses identify sites of differential DNA methylation in normal and transformed human cells. Nat Genet. Aug. 2005;37(8):853-62. Epub Jul. 10, 2005.
Wei et al., A global map of p53 transcription-factor binding sites in the human genome. Cell. Jan. 13, 2006;124(1):207-19.
Weinman et al., Isolating human transcription factor targets by coupling chromatin immunoprecipitation and CpG island microarray analysis. Genes Dev. Jan. 15, 2002; 16(2): 235-244. doi: 10.1101/gad.943102.
Zeng et al., High-Performance Single Cell Genetic Analysis Using Microfluidic Emulsion Generator Arrays. Anal Chem. Apr. 15, 2010;82(8):3183-90.
Zhang et al., A surface topography assisted droplet manipulation platform for biomarker detection and pathogen identification. Lab Chip. Feb. 7, 2011;11(3):398-406.
Zhang et al., Modeling ChIP sequencing in silicon with applications. PLoS Comput Biol. Aug. 22, 2008;4(8):e1000158. doi: 10.1371/journal.pcbi.1000158.
Zilionis et al., Single-cell barcoding and sequencing using droplet microfluidics. Nat Protoc. Jan. 2017;12(1):44-73. doi: 10.1038/nprot.2016.154. Epub Dec. 8, 2016.
EP 18215320.5, Mar. 14, 2019, Extended European Search Report.
JP 2017-506636, Apr. 2, 2019, Japanese Office Action.
EP 17198030.3, Mar. 21, 2019, European Office Action.
JP 2016-564093, Mar. 19, 2019, Japanese Office Action.
Office Action dated Apr. 29, 2019 for U.S. Appl. No. 15/303,874.
Office Action dated May 6, 2019 for U.S. Appl. No. 15/303,893.
Office Action dated May 1, 2079 for U.S. Appl. No. 15/723,490.
The following is a concise explanation of the relevance of each non-English language reference listed on the attached form PTO-1449 (modified PTO/SB/08).
The relevance of JP 2007-503984 can be understood its figures and by what is believed to be its English-language counterpart, WO 2005/021151, which has been previously cited.
The relevance of JP 2010-520749 can be understood its figures and by what is believed to be its English-language counterpart, WO 2008/127789, cited herein.
The relevance of JP 2010-193884 can be understood its figures and by what is believed to be its English-language counterpart, US 2010-0248237, cited herein.

The relevance of JP 2011-509075 can be understood its figures and by what is believed to be its English-language counterpart, WO 2009/085215, which has been previously cited.
The relevance of JP 2015-528283 can be understood its figures and by what is believed to be its English-language counterpart, WO 2014/028537, cited herein.
The relevance of WO 2013/011611 can be understood its English-language abstract and figures and by what is believed to be its English-language counterpart, US 2014-0200162, cited herein.
Extended European Search Report for Application No. EP 18215320.5 dated Mar. 14, 2019.
Japanese Office Action dated Apr. 2, 2019 for Application No. JP 2017-506636.
European Office Action dated Mar. 21, 2019 for Application No. 17198030.3.
Japanese Office Action dated Mar. 19, 2019 for Application No. JP 2016-564093.
Office Action dated May 1, 2019 for U.S. Appl. No. 15/723,490.
Office Action dated Nov. 22, 2019 for U.S. Appl. No. 15/303,874.
Office Action dated Aug. 6, 2019, for U.S. Appl. No. 14/734,903.
Office Action dated Aug. 29, 2019 for U.S. Appl. No. 15/556,904.
U.S. Appl. No. 14/734,903, filed Jun. 9, 2015, Weitz el al.
EP 17201280.9, Oct. 9, 2019, European Office Action.
EP 15780364.4, Aug. 29, 2019, European Office Action.
EP 17201280.9, Oct. 1, 2019 European Office Action.
JP 2016-564093, Nov. 26, 2019, Japanese Office Action.
EP 16780825.2, Dec. 16, 2019, European Office Action.
European Office Action dated Oct. 9, 2019 for Application No. EP 17201280.9.
European Office Action dated Aug. 29, 2019 for Application No. EP 15780364.4.
European Office Action dated Oct. 1, 2019 for Application No. EP 18201501.6.
Japanese Office Action dated Nov. 26, 2019 for Application No. JP 2016-564093.
European Office Action dated Dec. 16, 2019 for Application No. EP 16780825.2.
European Office Action for Application No. EP 13758373.8 dated Oct. 12, 2017.
European Office Action for Application No. EP 3758373.8 dated Apr. 24, 2018.
European Search Report for Application No. EP 17201280.9 dated Feb. 12, 2018.
Extended European Search Report for Application No. EP 17201280.9 dated May 23, 2018.
Chinese Office Action dated Jan. 28, 2019 for Application No. 201580029304.3
Extended European Search Report for Application No. EP 15780044.2 dated Oct. 26, 2017.
European Communication dated Sep. 4, 2018 for Application No. EP15780044.2.
Chinese Office Action dated Nov. 29, 2018 for Application No. 201580029045.4.
Extended European Search Report for Application No. EP 15780364.4 dated Oct. 23, 2017.
European Communication dated Sep. 4, 2018 for Application No. EP15780364.4.
Australian Examination Report dated Sep. 25, 2018 for Application No. 2015250034.
Extended European Search Report for Application No. EP 15783629.7 dated Nov. 17, 2017.
European Office Communication dated Jul. 6, 2018. For Application No. EP 15783629.7.
Extended European Search Report for Application No. EP 17198030.3 dated Jan. 19, 2018.
European Office Action dated Oct. 22, 2018 for Application No. 17198030.3.
Extended European Search Report dated Jan. 21, 2019 for Application No. 18201501.6.
Extended European Search Report dated Aug. 1, 2018 for Application No. 16780825.
International Preliminary Report on Patentability for Application No. PCT/US2016/027734 dated Oct. 26, 2017.

(56) References Cited

OTHER PUBLICATIONS

International Search Report and Written Opinion for Application No. PCT/US2017/043660 dated Nov. 6, 2017.
International Preliminary Report on Patentability dated Feb. 7, 2019 for Application No. PCT/US2017/043660.
Adli et al., Genome-wide chromatin maps derived from limited numbers of hematopoietic progenitors. Nat Methods. Aug. 2010;7(8):615-8.
Clausell-Tormos et al., Droplet-based microfluidic platforms for the encapsulation and screening of Mammalian cells and multicellular organisms. Chem Biol. May 2008;15(5):427-37. doi: 1016/j.chembiol.2008.04.004. Erratum in: Chem Biol.Aug. 25, 2008;15(8):875.
Cloonan et al. Stem cell transcriptome profiling via massive-scale mRNA sequencing. Nat Methods. Jul. 2008;5(7):613-9. doi: 10.1038/nmeth.1223. Epub May 30, 2008.
Eastburn Ultrahigh-throughput Mammalian single-cell reverse-transcriptase polymerase chain reaction in microfluidic drops. Anal Chem. Aug. 20, 2013:85(16):8016-21. doi: 10.1021/ac402057q. Epub Aug. 8, 2013. PubMed PMID: 23885761.
Islam et al. Characterization of the single-cell transcriptional landscape by highly multiplex RNA-seq.Genome Research.2011.(21)1160-1167.
Islam et al., Quantitative single-cell RNA-seq with unique molecular identifiers. Nat Methods. Feb. 2014;11(2):163-6. doi:10.1038/nmeth.2772. Epub Dec. 22, 2013.
Kalisky et al. Single-cell genomics. Nat Methods. Apr. 2011;8(4):311-4. doi: 10.1038/nmeth0411-311.
Klein et al. Comparative genomic hybridization, loss of heterozygosity, and DNA sequence analysis of single cells. Proc Natl Acad Sci U S A. Apr. 13, 1999;96(8):4494-9.
Mazutis et al., Single-cell analysis and sorting using droplet-based microfluidics. Nat Protoc. May 2013;8(5):870-91. doi: 10.1038/nprot.2013.046. Epub Apr. 4, 2013.
Okochi et al. Droplet-based gene expression analysis using a device with magnetic force-based-droplet-handling system. J of Bioscience and Bioengeneering.2010.(109)193-197.
O'Neill et al. Epigenetic characterization of the early embryo with a chromatin immunoprecipitation protocol applicable to small cell populations. Nat Genet. Jul. 2006;38(7):835-41. Epub Jun. 11, 2006.
O'Neill et al., Immunoprecipitation of native chromatin: NChIP. Methods. Sep. 2003;31(1):76-82.
Park et al.. ChIP-seq: Advantages and challenges of a maturing technology. Nat Rev Genetics. Oct. 1, 2009; 10(10):669-680.
Rizzo et al., Standardized collection of MNase-seq experiments enables unbiased dataset comparisons. BMC Mol Biol. May 6, 2012;13:15.
Rotem et al. Single-cell ChIP-seq reveals cell subpopulations defined by chromatin state. Nature Biotechnology. 2015. (33)1165-1175.
Tang et al.RNA-Seq analysis to capture the transcriptome landscape of a single cell. Nat Protoc. Mar. 2010:5(3):516-35. doi: 10.1038/nprot.2009.236. Epub Feb. 25, 2010.
Teh et al., Droplet microfluidics. Lab Chip. Feb. 2008;8(2):I 98-220. doi: 10.1039/13715524g. Epub Jan. 11, 2008.
Vigneault et al. Efficient microRNA capture end bar-coding via enzymatic oligonucleotide adenylation. Nature Methods.2008.(5):777-779.
Wal et al.. Genome-wide mapping of nucleosome positions in yeast using high-resolution MNase ChIP-Seq. Methods Enzytnol. 2012:513:233-50.
Zhang et al., High-resolution genome-wide mapping of the primary structure of chromatin. Cell. Jan. 21, 2011;144(2):175-86.
U.S. Appl. No. 15/723,490, filed Oct. 3, 2017, Weitz et al.
U.S. Appl. No. 15/670,929, filed Aug. 7, 2017, Rotem et al.
EP 13758373.8, Nov. 24, 2015, Extended European Search Report.
EP 13758373.8, Nov. 18, 2016, European Office Action.
PCT/US2013/029123, May 23, 2013, International Search Report and Written Opinion.
PCT/US2013/029123, Sep. 18, 2014, International Preliminary Report on Patentability.
PCT/US2015/026338, Sep. 8, 2015, International Search Report and Written Opinion.
PCT/US2015/026338, Oct. 27, 2016, International Preliminary Report on Patentability.
PCT/US2015/026422, Sep. 2, 2015, International Search Report and Written Opinion.
PCT/US2015/026422, Oct. 27, 2016, International Preliminary Report on Patentability.
PCT/US2015/026443, Jul. 27, 2015, International Search Report and Written Opinion.
PCT/US2015/026443, Nov. 3, 2016, International Preliminary Report on Patentability.
PCT/US2016/027734, Jul. 14, 2016, International Search Report and Written Opinion.
Office Action dated Sep. 24, 2015 for U.S. Appl. No. 14/734,903.
Office Action dated Feb. 1, 2016 for U.S. Appl. No. 14/734,903.
Advisory Action dated May 19, 2016 for U.S. Appl. No. 14/734,903.
Office Action dated Oct. 7, 2016 for U.S. Appl. No. 14/734,903.
Office Action dated Apr. 14, 2017 for U.S. Appl. No. 14/734,903.
Advisory Action dated Aug. 2, 2017 for U.S. Appl. No. 14/734,903.
Office Action dated Sep. 12, 2017 for U.S. Appl. No. 14/734,903.
Office Action dated Jun. 2, 2016 for U.S. Appl. No. 14/478,672.
Office Action dated Dec. 29, 2016 for U.S. Appl. No. 14/478,672.
Notice of Allowance dated Jun. 14, 2017 for U.S. Appl. No. 14/478,672.
EP 13758373.8, Oct. 12, 2017, European Office Action.
EP 13758373.8, Apr. 24, 2018, European Office Action.
EP17201280.9, Feb. 12, 2018, European Search Report.
EP 17201280.9, May 23, 2018, Extended European Search Report.
201580029304.3, Jan. 28, 2019, Chinese Office Action.
EP 15780044.2, Oct. 26, 2017, Extended European Search Report.
EP15780044.2, Sep. 4, 2018, European Office Action.
201580029045.40, Nov. 29, 2018, Chinese Office Action.
EP 15780364.4, Oct. 23, 2017, Extended European Search Report.
EP15780364.4, Sep. 4, 2018, European Office Action.
AU 2015250034, Sep. 25, 2018, Australian Examination Report.
EP 15783629.7, Nov. 17, 2017, Extended European Search Report.
EP 15783629.7, Jul. 6, 2018, European Office Action.
EP 17198030.3, Jan. 19, 2018, Extended European Search Report.
EP 17198030.3, Oct. 22, 2018, European Office Action.
EP 18201501.6, Jan. 21, 2019, European Search Report.
EP 16780825, Aug. 1, 2018, Extended European Search Report.
PCT/US2016/027734, Oct. 26, 2017, International Preliminary Report on Patentability.
PCT/US2017/043660, Nov. 6, 2017, International Search Report and Written Opinion.
PCT/US2017/043660, Feb. 7, 2019, International Preliminary Report on Patentability.
Office Action dated Oct. 6, 2017 for U.S. Appl. No. 15/303,874.
Final Office Action dated Jun. 22, 2018 for U.S. Appl. No. 15/303,874.
Office Action dated Oct. 6, 2017 for U.S. Appl. No. 15/303,893.
Office Action dated May 17, 2018 for U.S. Appl. No. 15/303,893.
Office Action dated Jul. 5, 2018 for U.S. Appl. No. 14/734,903.
Office Action dated Feb. 12, 2019 for U.S. Appl. No. 14/734,903.
Office Action dated Apr. 30, 2018 for U.S. Appl. No. 15/723,490.
Office Action dated Nov. 14, 2018 for U.S. Appl. No. 15/723,490.
Advisory Action dated Feb. 14, 2019 for U.S. Appl. No. 15/723,490.
Office Action dated Nov. 17, 2017 for U.S. Appl. No. 14/478,672.
Office Action dated Jun. 5, 2018 for U.S. Appl. No. 14/478,672.
Office Action dated Dec. 6, 2018 for U.S. Appl. No. 14/478,672.
European Office Action for Application No. EP 18215320.5 dated Nov. 11, 2020.
Australian Examination Report dated Sep. 11, 2020 for Application No. AU 2015247416.
Canadian Office Action dated Jan. 28, 2021 for Application No. CA 2945798.
Chinese Office Action dated Jan. 20, 2021 for Application No. 201580029081.0.
European Office Action dated Oct. 21, 2020 for Application No. 18201501.6.
European Office Action dated Aug. 21, 2020 for Application No. EP 16780825.2.
Office Action dated Nov. 13, 2020 for U.S. Appl. No. 14/734,903.

(56) References Cited

OTHER PUBLICATIONS

U.S. Appl. No. 15/303,874, filed Oct. 13, 2016, Bernstein et al.
U.S. Appl. No. 15/303,893, filed Oct. 13, 2016, Weitz et al.
U.S. Appl. No. 14/734,903, filed Jun. 9, 2015, Weitz et al.
U.S. Appl. No. 15/991,600, filed May 29, 2018, Weitz et al.
U.S. Appl. No. 14/178,672, filed Sep. 5, 2014, Rotem et al.
U.S. Appl. No. 15/836,479, filed Dec. 8, 2017, Weitz et al.
U.S. Appl. No. 15/836,520, filed Dec. 8, 2017, Weitz et al.
U.S. Appl. No. 15/965,452, filed Apr. 27, 2018, Weitz et al.
U.S. Appl. No. 15/566,904, filed Oct. 16, 2017, Weitz et al.
EP 18215320.5 dated Nov. 10, 2020, European Office Action.
AU 2015247416 dated Sep. 11, 2020, Australian Examination Report.
CA 2945798 dated Jan. 28, 2021, Canadian Office Action.
CN 20158002908.1 dated Jan. 20, 2021, Chinese Office Action.
EP 18201501.6 dated Oct. 21, 2020, European Office Action.
EP 16780825.2 dated Aug. 21, 2020, European Office Action.

* cited by examiner

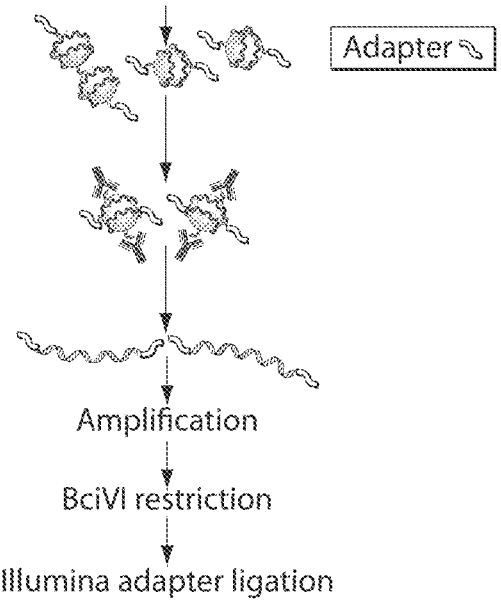
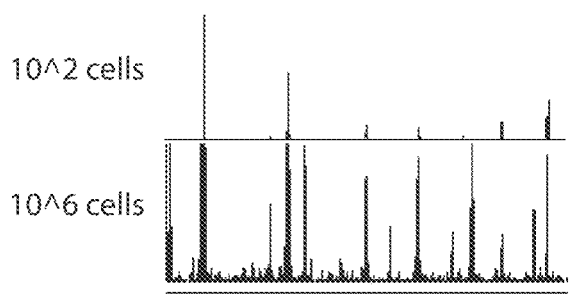
Fig. 1C

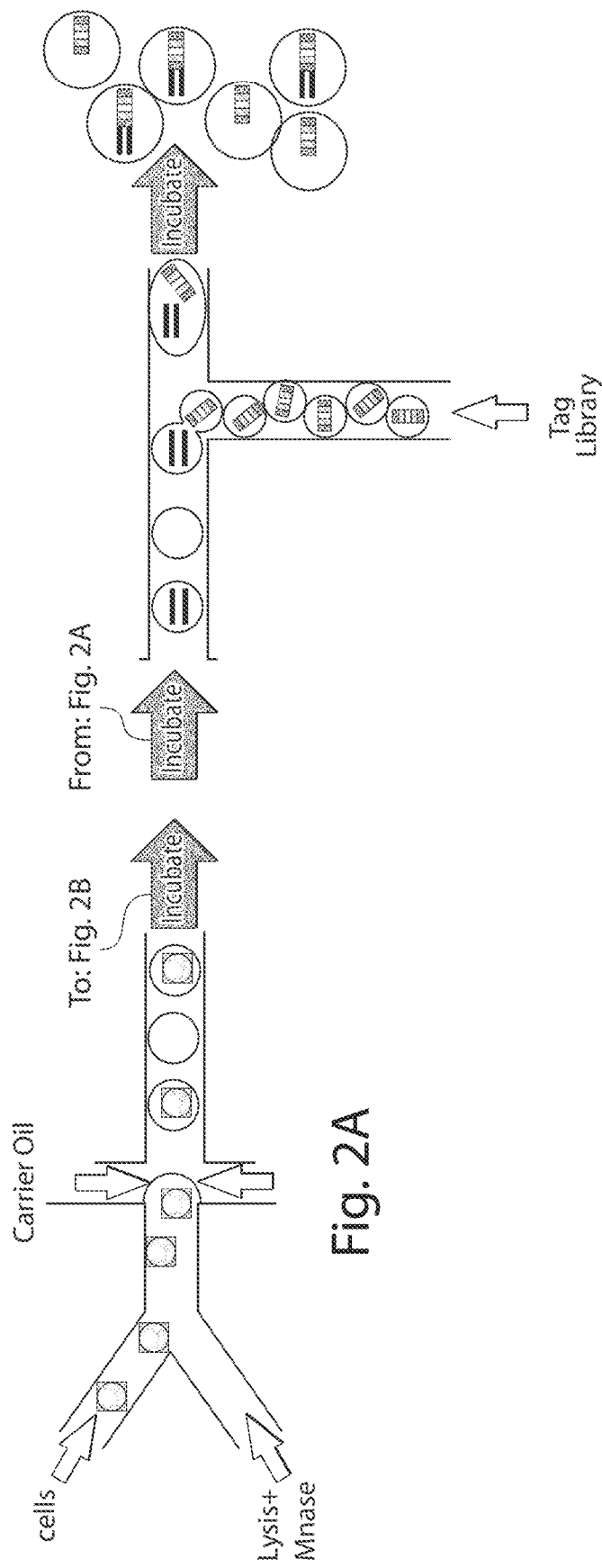

SYSTEMS AND METHODS FOR EPIGENETIC SEQUENCING

RELATED APPLICATIONS

This application is a continuation of U.S. patent application Ser. No. 14/478,672, filed Sep. 5, 2014, entitled "Systems and Methods for Epigenetic Sequencing," by Rotem, et al., which is a continuation-in-part of Int. Patent Application No. PCT/US2013/029123, filed Mar. 5, 2013, entitled "Systems and Methods for Epigenetic Sequencing," by Rotem, et al., which claims the benefit of U.S. Provisional Application Ser. No. 61/634,744, filed Mar. 5, 2012, entitled "Systems and Methods for Epigenetic Sequencing," by Rotem, et al., each incorporated herein by reference.

GOVERNMENT FUNDING

This invention was made with government support under HG004570 awarded by the National Institutes of Health. The government has certain rights in the invention.

FIELD OF INVENTION

The present invention generally relates to microfluidics and/or epigenetic sequencing.

BACKGROUND

Epigenetics is the study of the transmission of genetic information by mechanisms other than the DNA sequence of nucleotides. For example, epigenetic information may be transmitted via methylation of nucleotides within DNA (e.g., cytosine to 5-methylcytosine), or by histone modifications such as histone acetylation or deacetylation, methylation, ubiquitylation, phosphorylation, sumoylation, etc. Such epigenetic modifications may affect the structure of chromatin, which is a higher-order structure of protein, DNA and RNA within cells. Chromatin structure is known to play an important role in regulating genome function and in particular, its varied structure across cell types helps ensure that the correct genes are expressed in the correct cell types.

Most techniques for studying epigenetics typically require large populations of cells, e.g., thousands of cells. For example, histone modifications can be mapped by immunoprecipitating chromatin with antibodies to a modified histone and then sequencing the DNA (ChIP-Seq). However, this method typically requires ~100,000 cells or more. Furthermore, the analysis is carried out on the entire population and is blind to differences among cells.

In contrast, however, systems and methods for studying the epigenomes in single cells or small numbers of cells are becoming increasingly important for understanding the principles of chromatin and genome regulation. Moreover, such approaches could have many clinical applications in cancer biology, immunology, neuroscience or other fields in which subject tissues are complex, heterogeneous and/or limited in size. For example, tumors represent heterogeneous mixtures of cells that may be driven by sub-populations of cancer stem cells. Single cell epigenomic profiling methods could improve understanding of critical epigenomic changes in cancer stem cells. They might also enable early detection or surveillance of disease.

SUMMARY

The present invention generally relates to microfluidics and/or epigenetic sequencing. The subject matter of the present invention involves, in some cases, interrelated products, alternative solutions to a particular problem, and/or a plurality of different uses of one or more systems and/or articles.

In one set of embodiments, the present invention is generally directed to a method comprising acts of providing a plurality of cells contained within a plurality of microfluidic droplets, lysing the cells contained within the microfluidic droplets to produce cell lysates therein, exposing at least some of the cell lysates contained within the microfluidic droplets to a non-nucleosome-cleaving nuclease to produce a plurality of nucleosome sequences within the microfluidic droplets, ligating adapters to at least some of the nucleosome sequences, the adapters comprising an identification sequence and a restriction site, and sequencing the nucleosome sequences containing ligated adapters.

In another set of embodiments, the present invention is generally directed to a method of providing a solution comprising a plurality of nucleosome sequences originating from a plurality of cells, at least some of the nucleosome sequences being ligated to an adapter, the adapter comprising an identification sequence and a restriction site, wherein nucleosome sequences originating from the same cell contain identical identification sequences, and nucleosome sequences originating from different cells contain different identification sequences, and sequencing at least some of the nucleosome sequences.

The present invention, in yet another set of embodiments, is generally directed to a composition comprising a plurality of droplets, at least some of which each contain a nucleosome sequence ligated to an adapter, the adapter comprising an identification sequence and a restriction site, wherein nucleosome sequences originating from the same cell contain identical identification sequences, and nucleosome sequences originating from different cells contain different identification sequences.

In still another set of embodiments the present invention is generally directed to a composition comprising a nucleic acid sequence comprising an identification sequence, a restriction site, an inversion of the restriction site, and an inversion of the identification sequence.

In another set of embodiments, the present invention is generally directed to a composition comprising a plurality of palindromic or substantially palindromic nucleic acid sequence comprising a plurality of different identification sequences each having the same length, and a substantially identical restriction site.

In another aspect, the present invention encompasses methods of making one or more of the embodiments described herein. In still another aspect, the present invention encompasses methods of using one or more of the embodiments described herein.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIGS. 1A-1C illustrate a method of epigenetic sequencing in accordance with certain embodiments of the invention;

FIGS. 2A-2B illustrate cells that are lysed and "tagged" with adapters, in another embodiment of the invention;

DETAILED DESCRIPTION

The present invention generally relates to microfluidics and/or epigenetic sequencing. In one set of embodiments, cells contained within a plurality of microfluidic droplets are lysed and the DNA (e.g., from nucleosomes) within the droplets are labeled, e.g., with adapters containing an identification sequence. The adapters may also contain other sequences, e.g., restriction sites, primer sites, etc., to assist with later analysis. After labeling with adapters, the DNA from the different cells may be combined and analyzed, e.g., to determine epigenetic information about the cells. For example, the DNA may be separated on the basis of certain modifications (e.g., methylation) using techniques such as chromatin immunoprecipitation ("ChIP"), and the DNA from the separated nucleosomes may be sequenced and aligned with genomes, e.g., to determine which portions of the genome were epigenetically modified, e.g., via methylation.

Thus, various aspects of the present invention are generally directed through DNA sequencing to determine epigenetic information. For instance, in one set of embodiments, cells contained within microfluidic droplets are lysed and their DNA is exposed to certain enzymes, such as non-nucleosome-cleaving nucleases or other enzymes that are able to cleave the DNA for later analysis without destroying certain types of epigenetic information, e.g., the interaction of the DNA with the histones, the methylation patterns within DNA, etc. The DNA (still contained within the microfluidic droplets) is then barcoded or tagged using a ligation step with specific "adapters" that can be used to later identify the source, down to a single cell level in some cases, of the DNA.

After ligation of the adapters to the DNA, the DNA may then be sequenced. In certain embodiments, droplets containing the lysate of different cells may be combined together prior to analysis. Due to the presence of the ligated adapters, the DNA originating from the same cell may contain identical identification sequences, while DNA originating from different cells may contain different identification sequences, thereby allowing the DNA of each cell within a sample to be separately identified and determined. In some cases, for instance, the identification sequences may be selected such that a certain number of cells taken from a plurality of cells can be readily identified. For example, an identification sequence of n nucleotides may allow for up to $4^n$ distinct cells to be studied. Thus, even relatively small identification sequences (e.g., 4, 5, 6, 7, 8, 9, etc. nucleotides long) may allow for relatively large populations of cells to be separately determined, e.g., at a single-cell level.

Figure 6:
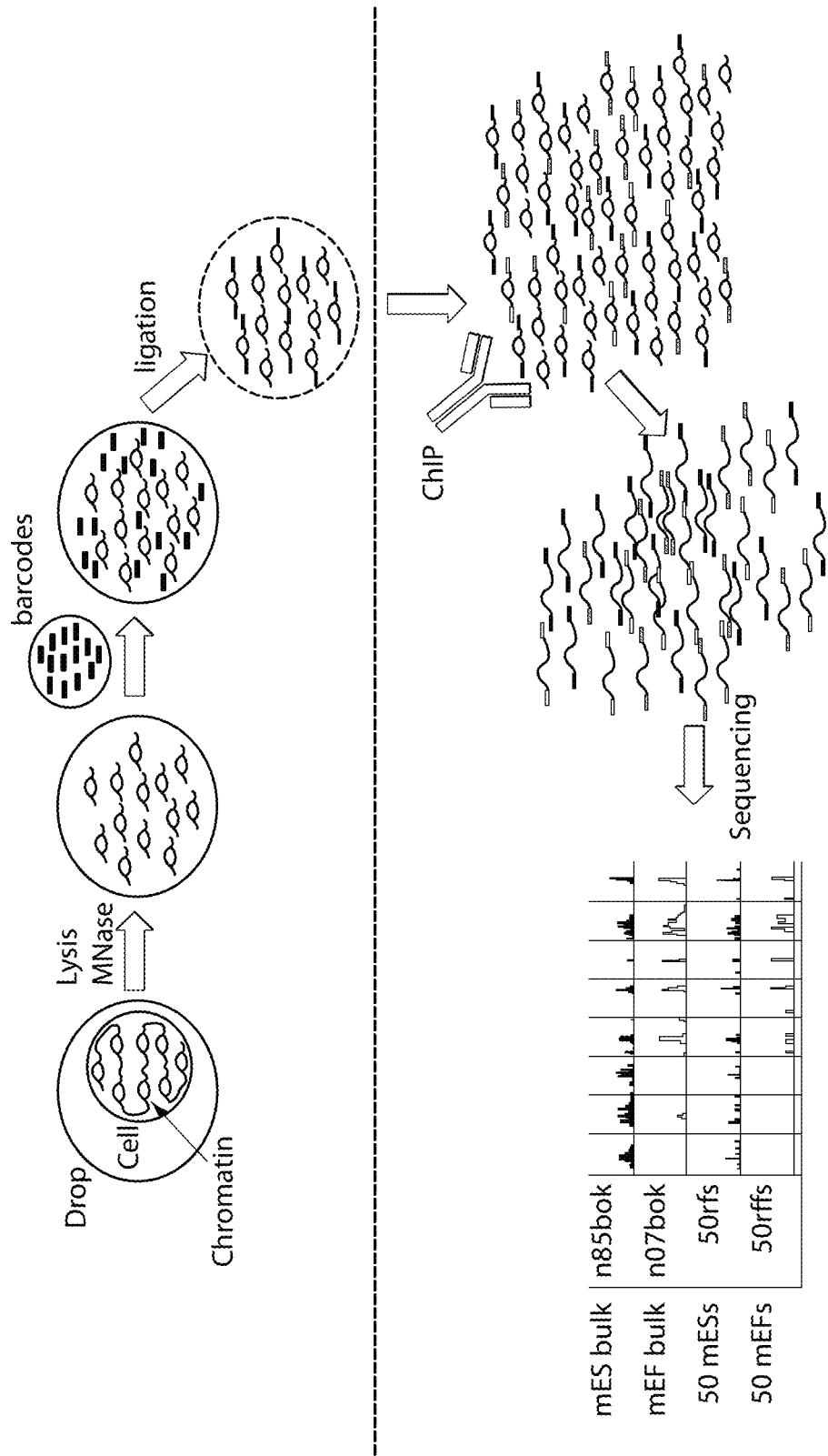
FIG. 6 illustrates ChIP sequencing technique, in accordance with still another embodiment of the invention.

One non-limiting example is illustrated with reference to FIG. 6. In this figure, a cell (containing chromatin) is contained within a microfluidic droplet. The cell is lysed and exposed to an enzyme such as MNase, which cleaves the DNA released from the lysed cell into smaller fragments without substantially affecting those portions of the DNA that interact with the histones within the nucleosome structures. Barcodes or other adapters, which may be formed from certain types of sequences as is discussed herein, are added to the droplet and ligated together. Next, ChIP analysis is performed and the DNA sequenced.

Figure 1A:
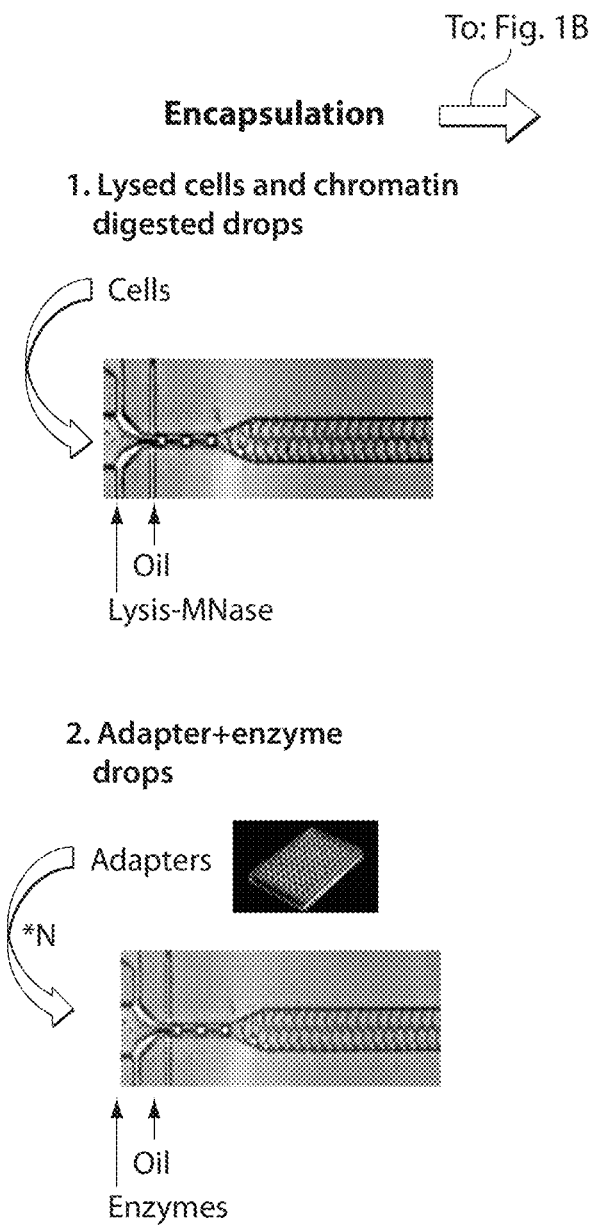

Another example of an embodiment of the invention is now described with respect to FIG. 1. In FIG. 1A, part 1, and in FIG. 2A, a plurality of cells are contained within droplets using a microfluidic droplet maker, e.g., within an aqueous environment contained within an oil. Typically, the cells are encapsulated within droplets at a density such that on average, each droplet contains one cell (or less). Within a droplet, a cell may be lysed, then exposed to an enzyme such as MNase, which cleaves the DNA released from the lysed cell into smaller fragments without substantially affecting those portions of the DNA that interact with the histones within the nucleosome structures. Droplets containing an adapter (as discussed below), a ligase, and/or other components such as buffers or the like are also created separately, as shown in FIG. 1A, part 2. Similar to FIG. 1A, part 1, the adapters may be contained in a droplet within an aqueous environment, contained within an oil.

Figure 1B:
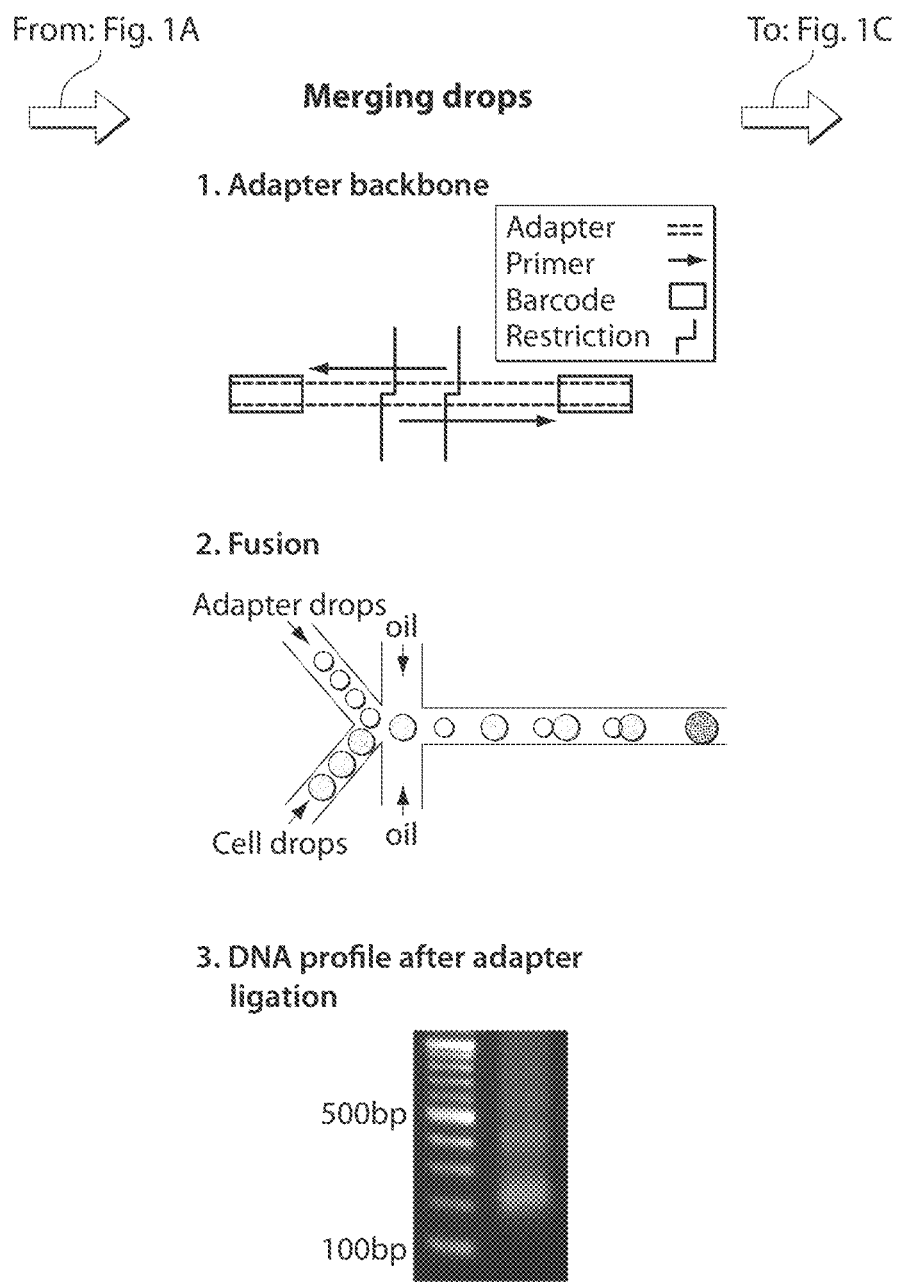
Figure 3:
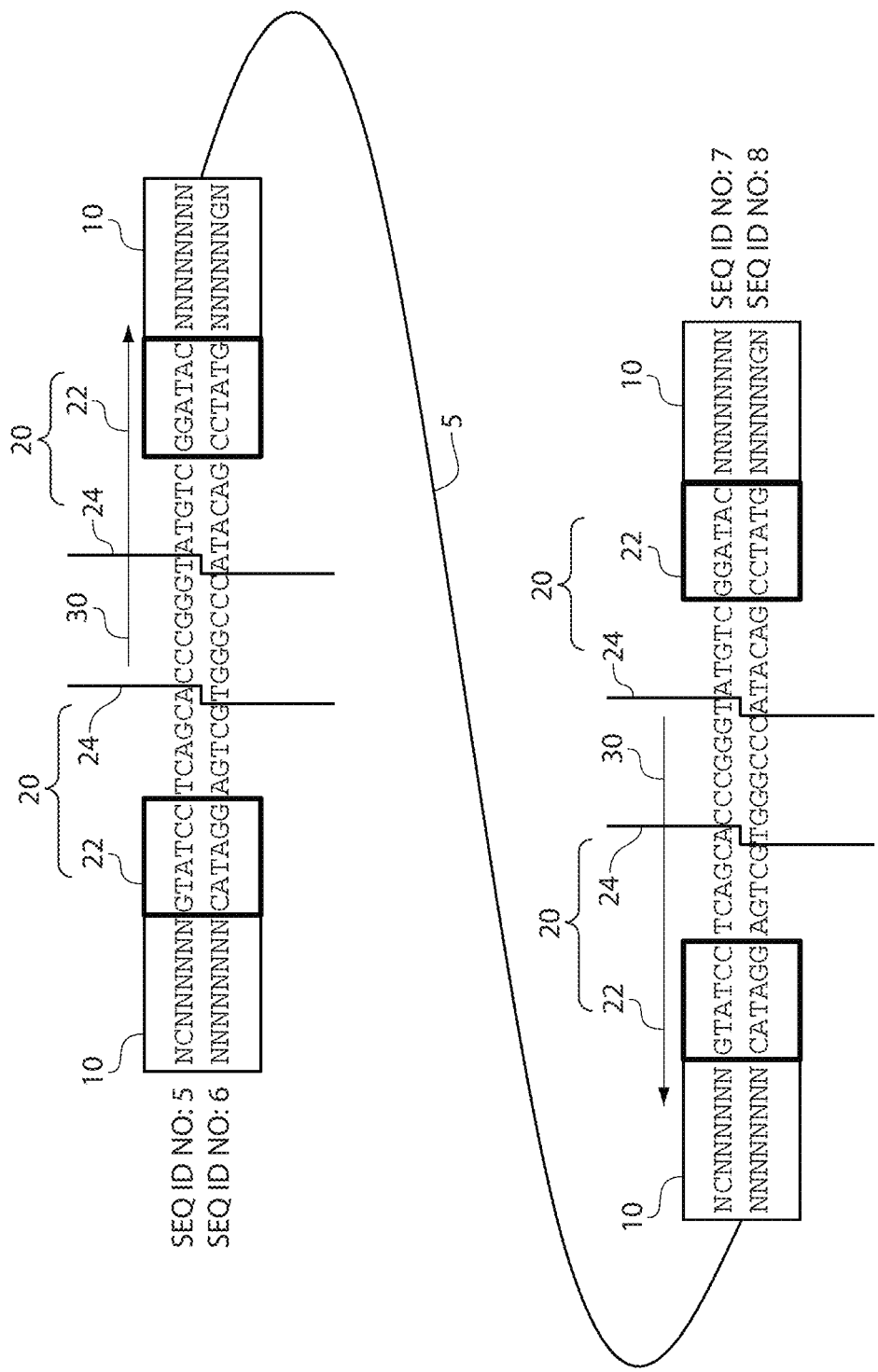
FIG. 3 illustrates the structure of an adapter, corresponding to SEQ ID NOs:5-8 top to bottom, in accordance with another embodiment of the invention.
Figure 4A:
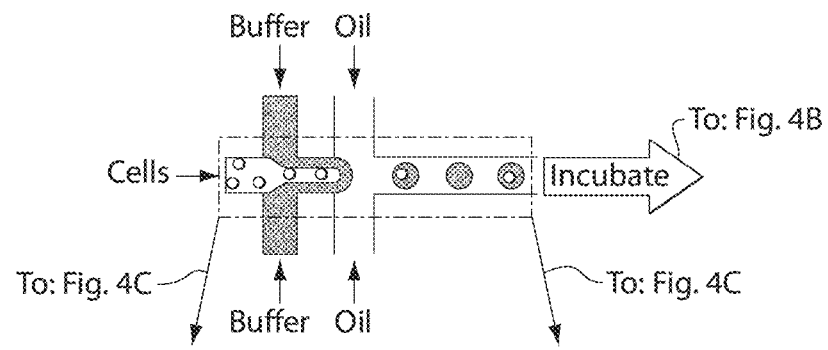
FIGS. 4A-4D illustrate cell preparation in another embodiment of the invention.
Figure 4B:
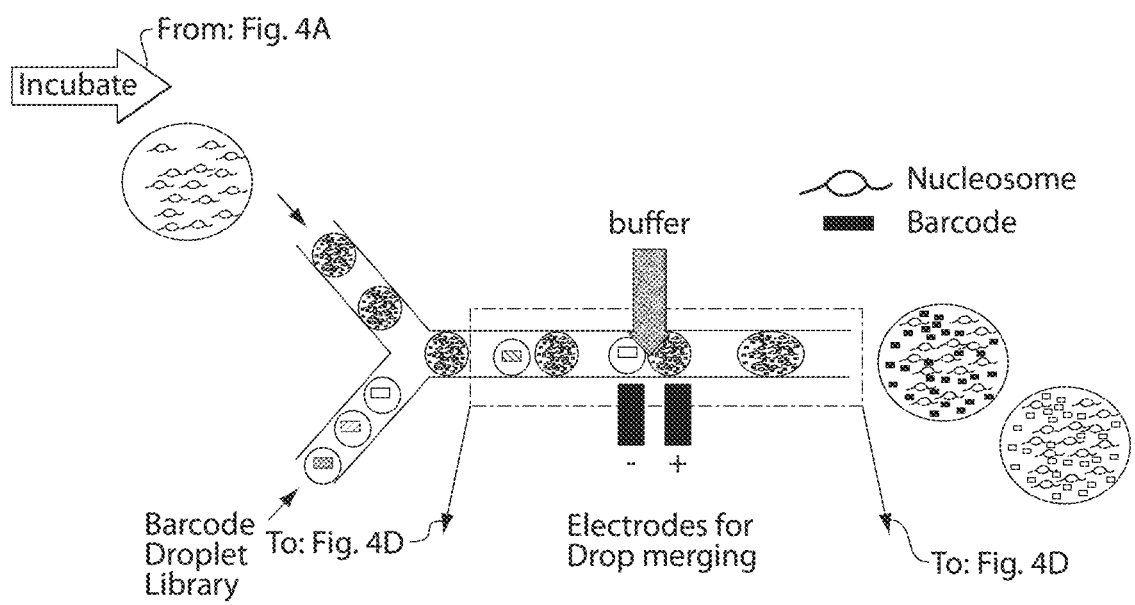
Figure 4C:
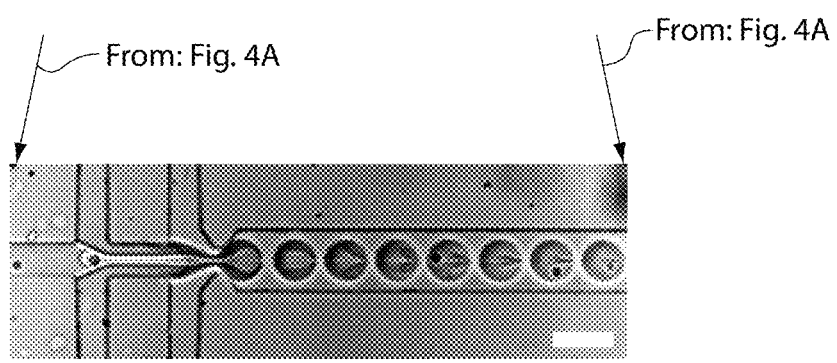
Figure 4D:

A schematic diagram of an example of an adapter is shown in FIG. 1B, part 1, and FIG. 3. The adapter in this example comprises a sequence recognizable by a primer (e.g., a PCR primer), a "barcode" or other identification sequence, and a restriction site that can be cleaved by a suitable restriction endonuclease. The identification site typically has 4-15 nucleotides, and for a population of adapters to be used to identify a population of cells, the identification sequence of the adapter may differ while the rest of the adapter is substantially constant. Accordingly, because each cell is exposed to an adapter containing a different identification sequence, the nucleic acids arising from these cells may be subsequently distinguished. In this example, the adapter is palindromic or at least substantially palindromic, so that the adapter further contains inverses of these, e.g., as part of a double-stranded structure.

For example, FIG. 3 shows the structure of a typical adapter attached to a length of DNA 5, including an identification region 10, a restriction site (including a recognition sequence 22 and a cleavage sequence 24), and a primer sequence 30. Note that DNA 5 in this example actually has two adapters, one on either side, having the same structure. Due to the generally palindromic nature of these adapters, the adapters cannot be added to the DNA incorrectly, as either orientation would be correct. In addition, in some embodiments, additional adapters could potentially be ligated onto the ends of the adapters. However, due to subsequent cleavage by a suitable restriction endonuclease at the cleavage site, any unwanted or extra adapters can be readily separated from the DNA itself, leaving just the identification sequence remaining on one or both ends, for subsequent determination or analysis.

The droplets containing the cells may be merged with the droplets containing the adapters, as is shown in FIG. 1B, part 2, as well as FIG. 2B (where the tag library is formed from the adapters). Various techniques may be used to fuse the droplets together, and typically, the droplets are fused in a 1:1 ratio such that a single cell (contained within a single droplet) is exposed to a unique adapter (i.e., containing a unique identification sequence). Within the droplets, the adapters are ligated to the DNA released from the lysed cells. As each droplet typically contains a unique adapter, the DNA in each droplet is uniquely identified by a unique identification sequence. A plurality of DNA molecules is typically found within each droplet, some or all of which are thus labeled by the same adapter.

Next, the DNA within the droplets may be sequenced or analyzed, as is shown in FIG. 1C, part 1. In some cases, DNA from different droplets may be combined together prior to analysis. As noted above, the presence of unique identification sequences on the adapters on the DNA may allow the DNA from each of the droplets to be analyzed and distinguished. Accordingly, for example, the DNA (and the epigenetic profile) from a first cell can be distinguished from the DNA from a second cell. Examples of unique identification sequences include those discussed in U.S. Pat. Apl. Ser. No. 61/703,848, incorporated herein by reference in its entirety.

In one set of embodiments, ChIP ("chromatin immunoprecipitation") may be used to analyze the DNA. For example, the DNA may be amplified (e.g., using PCR via the primer sequences), cleaved (e.g., using a restriction endonuclease that cleaves the adapter site, for instance, BciVI as is shown in this example), and/or ligated (e.g. using Illumina) such that the DNA is sequenced. A non-limiting example of such analysis is shown schematically in FIG. 1C, part 2. In this example, a plurality of cells may each be uniquely identified (for instance, upon selection of a suitable of nucleotides within the identification sequence), e.g., even for populations of 100 cells, 1 million cells, etc. However, it should be understood that other techniques could also be used for sequencing.

The above discussion is a non-limiting example of an embodiment of the present invention that can be used to determine an epigenetic profile of a cell. However, other embodiments are also possible. Accordingly, more generally, various aspects of the invention are directed to various systems and methods for sequencing the DNA of cells (typically contained within droplets) to determine epigenetic information.

In one aspect, microfluidic droplets are used, for example, to contain cells. Microfluidic droplets may be used to keep the cells of a plurality of cells separate and identifiable, e.g., such that epigenetic or genetic differences between the different cells may be identified. In contrast, in many prior art techniques, a plurality or a population of different cells may be studied for epigenetic differences, but there is no ability to determine those epigenetic differences on the level of an individual cell; instead, only average epigenetic profiles of those cells can be determined. In contrast, in certain embodiments of the present invention, a plurality of cells, some or all of which may contain individual epigenetic differences, may be studied, at resolutions down to the single-cell level, for example, within microfluidic droplets or other compartments or solutions such as those discussed herein.

The cells may arise from a human, or from a non-human animal, for example, an invertebrate cell (e.g., a cell from a fruit fly), a fish cell (e.g., a zebrafish cell), an amphibian cell (e.g., a frog cell), a reptile cell, a bird cell, or a mammal cell, such as a monkey, ape, cow, sheep, goat, horse, donkey, camel, llama, alpaca, rabbit, pig, mouse, rat, guinea pig, hamster, dog, cat, etc. If the cell is from a multicellular organism, the cell may be from any part of the organism. In some embodiments, a tissue may be studied. For example, a tissue from an organism may be processed to produce cells (e.g., through tissue homogenization or by laser-capturing the cells from the tissue), such that the epigenetic differences within the tissue may be determined, as discussed herein.

The cells or tissues may arise from a healthy organism, or one that is diseased or suspected of being diseased. For example, blood cells from an organism may be removed and studied to determine epigenetic differences or changes in the epigenetic profile of those cells, e.g., to determine if the animal is healthy or has a disease, for example, if the animal has cancer (e.g., by determining cancer cells within the blood). In some cases, a tumor may be studied (e.g., using a biopsy), and the epigenetic profile of the tumor may be determined. For instance, the cells may be studied to determine if any of the cells are cancer stem cells.

The cells may also be determined using other techniques, in addition to the ones discussed herein, which may assist in determining the epigenetic profile of the cells. For example, the cells may be studied using flow cytometry, microscopy, the cells may be cultured, etc., to determine whether the epigenetic profile (or changes in the epigenetic profile) correlate to other changes in the cell, for example, expression levels of a protein, changes in morphology, ability to reproduce or differentiate, etc.

In some aspects of the invention, a plurality of cells is contained within a plurality of droplets or other compartments. In some cases, the encapsulation rate may be kept low, for example, such that the average density is about 1 cell/droplet or compartment, or less. (In other cases, higher densities are also possible, of course, e.g., greater than 1 cell/droplet or compartment.) For example, the average density may be less than about 0.95 cells/droplet or compartment, less than about 0.9 cells/droplet or compartment, less than about 0.8 cells/droplet or compartment, less than about 0.7 cells/droplet or compartment, less than about 0.6 cells/droplet or compartment, less than about 0.5 cells/droplet or compartment, less than about 0.4 cells/droplet or compartment, less than about 0.3 cells/droplet or compartment, or less than about 0.2 cells/droplet or compartment. In some cases, the cells are contained such that no more than about 25%, no more than about 15%, no more than about 10% no more than about 5%, no more than about 3%, or no more than about 1% of the droplets or compartments contains more than one cell therein. Such relatively low densities may be useful, e.g., to avoid confusion of having more than one cell labeled with the same identification sequence (e.g., such that the DNA of the cell is ligated to an adapter), as discussed below.

The droplets may be contained in a microfluidic channel. For example, in certain embodiments, the droplets may have an average dimension or diameter of less than about 1 mm, less than about 500 micrometers, less than about 300 micrometers, less than about 200 micrometers, less than about 100 micrometers, less than about 75 micrometers, less than about 50 micrometers, less than about 30 micrometers, less than about 25 micrometers, less than about 10 micrometers, less than about 5 micrometers, less than about 3 micrometers, or less than about 1 micrometer in some cases.

The average diameter may also be at least about 1 micrometer, at least about 2 micrometers, at least about 3 micrometers, at least about 5 micrometers, at least about 10 micrometers, at least about 15 micrometers, or at least about 20 micrometers in certain instances. The droplets may be spherical or non-spherical. The average diameter or dimension of a droplet, if the droplet is non-spherical, may be taken as the diameter of a perfect sphere having the same volume as the non-spherical droplet.

The droplets may be produced using any suitable technique. For example, a junction of channels may be used to create the droplets. The junction may be, for instance, a T-junction, a Y-junction, a channel-within-a-channel junction (e.g., in a coaxial arrangement, or comprising an inner channel and an outer channel surrounding at least a portion of the inner channel), a cross (or "X") junction, a flow-focus junction, or any other suitable junction for creating droplets. See, for example, International Patent Application No. PCT/US2004/010903, filed Apr. 9, 2004, entitled "Formation and Control of Fluidic Species," by Link, et al., published as WO 2004/091763 on Oct. 28, 2004, or International Patent Application No. PCT/US2003/020542, filed Jun. 30, 2003, entitled "Method and Apparatus for Fluid Dispersion," by Stone, et al., published as WO 2004/002627 on Jan. 8, 2004, each of which is incorporated herein by reference in its entirety. In some embodiments, the junction may be configured and arranged to produce substantially monodisperse droplets.

In some cases, the cells may be encapsulated within the droplets at a relatively high rate. For example, the rate of cell encapsulation in droplets may be at least about 10 cells/s, at least about 30 cells/s, at least about 100 cells/s, at least about 300 cells/s, at least about 1,000 cells/s, at least about 3,000 cells/s, at least about 10,000 cells/s, at least about 30,000 cells/s, at least about 100,000 cells/s, at least about 300,000 cells/s, or at least about $10^6$ cells/s.

The droplets may be substantially monodisperse in some embodiments, or the droplets may have a homogenous distribution of diameters, e.g., the droplets may have a distribution of diameters such that no more than about 10%, no more than about 5%, no more than about 3%, no more than about 2%, or no more than about 1% of the droplets have a diameter less than about 90% (or less than about 95%, less than about 97%, or less than about 99%) and/or greater than about 110% (or greater than about 101%, greater than about 103%, or greater than about 105%) of the overall average diameter of the plurality of droplets. In some embodiments, the plurality of droplets has an overall average diameter and a distribution of diameters such that the coefficient of variation of the cross-sectional diameters of the droplets is less than about 10%, less than about 5%, less than about 2%, between about 1% and about 10%, between about 1% and about 5%, or between about 1% and about 2%. The coefficient of variation may be defined as the standard deviation divided by the mean, and can be determined by those of ordinary skill in the art.

In some embodiments, the fluid forming the droplets is substantially immiscible with the carrying fluid surrounding the droplets. For example, the fluid may be hydrophilic or aqueous, while the carrying fluid may be hydrophobic or an "oil," or vice versa. Typically, a "hydrophilic" fluid is one that is miscible with pure water, while a "hydrophobic" fluid is a fluid that is not miscible with pure water. It should be noted that the term "oil," as used herein, merely refers to a fluid that is hydrophobic and not miscible in water. Thus, the oil may be a hydrocarbon in some embodiments, but in other embodiments, the oil may be (or include) other hydrophobic fluids (for example, octanol). It should also be noted that the hydrophilic or aqueous fluid need not be pure water. For example, the hydrophilic fluid may be an aqueous solution, for example, a buffer solution, a solution containing a dissolved salt, or the like. A hydrophilic fluid may also be, or include, for example, ethanol or other liquids that are miscible in water, e.g., instead of or in addition to water.

In one aspect, after the cells are contained or encapsulated within droplets or other compartments, the cells may be lysed or otherwise processed to release the DNA within the cells, e.g., as a plurality of nucleosome sequences. Typically, the nucleosome sequences are those regions of the DNA that interact with the histones. The nucleosome sequence of the DNA typically winds around one or more histones to produce the basic nucleosome structure, which is subsequently packaged within the chromatin of the cell. For example, the cells may be lysed within the droplets by sonication (exposure to ultrasound), temperature or osmotic changes, exposure to certain types of enzymes or chemicals (for example, detergents such as Triton, e.g., Triton X-100), or the like. Those of ordinary skill in the art will be aware of suitable techniques for lysing cells to produce a cell lysate. Typically, the cells are lysed within the droplets without breaking down the droplets themselves, e.g., such that the cell lysate that is subsequently produced remains within the droplets.

The DNA may also be exposed to enzymes which are able to process the DNA without substantially affecting the epigenetic information of interest, e.g., without substantially altering the methylation of nucleotides within the DNA, without altering any histone modifications that might be present, etc. For example, in one set of embodiments, the DNA may be exposed to a non-nucleosome-cleaving nuclease able to cleave the DNA at regions other than where the DNA is contained within a nucleosome. Such a nuclease may accordingly be able to cleave the DNA into smaller fragments that can be subsequently analyzed (e.g., as discussed herein), without substantially affecting those portions of the DNA that interact with the histones within the nucleosome structures (i.e., the nucleosome sequences within the DNA). Accordingly, epigenetic information contained within the nucleosome structures may be preserved for subsequent determination. One example of a suitable enzyme is MNase (S7 nuclease or micrococcal nuclease), which is available commercially. In some cases, a restriction enzyme that targets a specific sequence may be used to digest genomic regions having particular sequence contents, such as GC-rich euchromatic loci.

In certain aspects, one or more adapters may be ligated or otherwise bonded onto the DNA (or RNA, in some embodiments). The adapter may be formed from DNA and/or RNA. The adapter may be single-stranded or double-stranded, and in some cases, the adapters may be palindromic or substantially palindromic, or in some cases the adapter can be single stranded. In one set of embodiments, the adapter may include an identification sequence and a restriction site (and/or a portion of a restriction site), and optionally a primer sequence. If the adapter is at least substantially palindromic, the adapter may also contain inversions of these, e.g., the adapter may contain an identification sequence, a restriction site, an inversion of the restriction site, and an inversion of the identification sequence.

One example of an adapter is shown in FIG. 7. In this example, adapter 70 includes a portion of a restriction site 71 ("site"), a first "barcode" or identification sequence 72, a second complete restriction site 73, a second "barcode" or identification sequence 74, and a second portion of a restriction site 75 ("restriction"). Adapter 70 also includes a region 76 that can be recognized by a primer. The adapter is joined to a stretch of nucleic acid, such as DNA 77, to be studied (e.g., containing a nucleosome 80 as is shown in FIG. 7, although this is just for explanatory purposes). In some cases, the first and second portions of the restriction site have the same sequence, e.g., for restriction sites that are palindromic in nature.

A restriction site is a site that is recognized by a restriction endonuclease. When the adapter is exposed to a restriction endonuclease that recognizes the restriction site, the restriction endonuclease may cleave the adapter within the restriction site. Those of ordinary skill in the art will be familiar with restriction endonucleases and restriction sites. The restriction endonuclease may cleave the restriction site to leave behind blunt ends or "sticky" ends (e.g., leaving an overhang with one or more nucleotides lacking a complement). The restriction site, in some cases, includes a recognition sequence (a specific sequence of nucleotides, e.g., 4, 5, 6, 7, or 8 nucleotides long) and a cleavage sequence that may be part of, or be separate from, the recognition sequence. For instance, with the BciVI restriction site, the restriction site includes a recognition sequence (which is 6 nucleotides in length as is shown in FIG. 3), where the restriction endonuclease recognizes the adapter, and a separate cleavage sequence where the restriction endonuclease actually cleaves the adapter (indicated by the jagged lines in FIG. 3). Those of ordinary skill in the art will be able to identify suitable restriction endonucleases and their restriction sites. Over 3000 restriction enzymes have been studied in detail, and more than 600 of these are available commercially. Non-limiting examples include BamHI, BsrI, NotI, XmaI, PspAI, DpnI, MboI, MnlI, Eco57I, Ksp632I, DraIII, AhaII, SmaI, MluI, HpaI, ApaI, BclI, BstEII, TaqI, EcoRI, SacI, HindII, HaeII, DraII, Tsp509I, Sau3AI, PacI, etc.

Figure 7A:
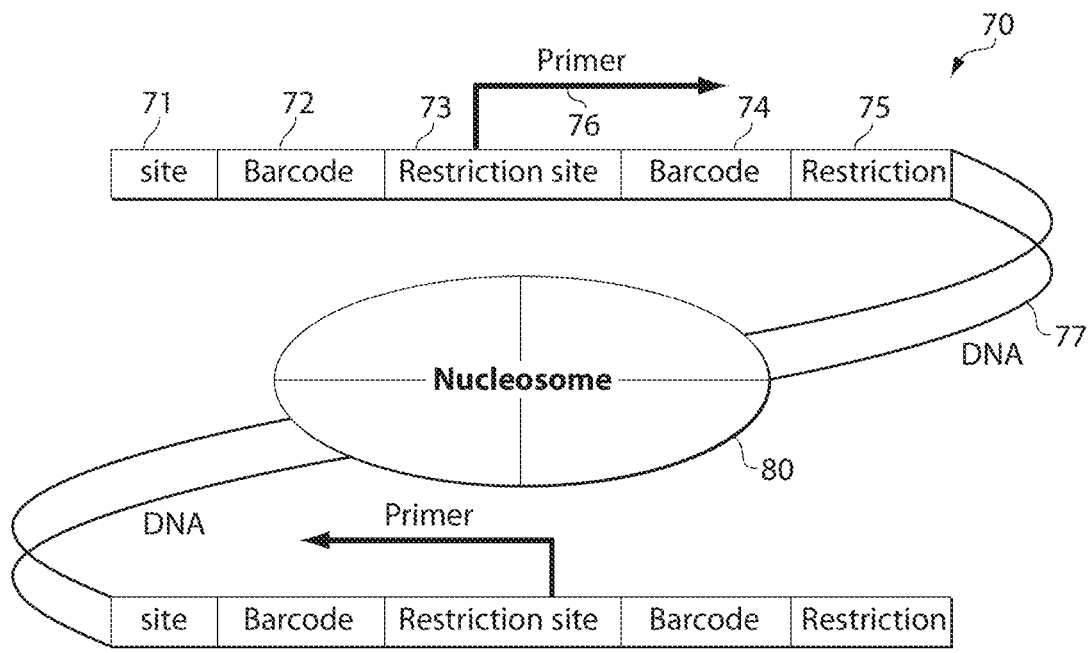
FIGS. 7A-7B illustrate adapters according to another embodiment of the invention.
Figure 7B:
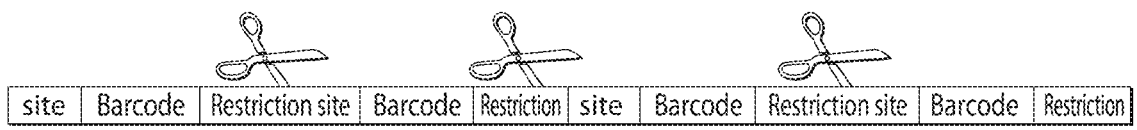

In one set of embodiments, an adaptor may contain a portion of a restriction site, e.g., first portions and second portions such that, when the first portion and the second portion are ligated or otherwise joined together, a complete restriction site. This may be useful, for example, in cases where an adapter is ligated to another adapter; the joined adapters, having a completed restriction site, may be exposed to a suitable corresponding restriction endonuclease that is able to cleave at the restriction site, thereby removing the extraneous adapters. A non-limiting example is shown schematically in FIG. 7. In FIG. 7A, a first portion of the restriction site is labeled "site" and a second portion is labeled "restriction." A corresponding restriction endonuclease will not recognize either portion, unless the portions are joined together to from a complete restriction site that can be recognized by the restriction endonuclease (i.e., forming the phrase "restriction site" in FIG. 7B).

As mentioned, in one set of embodiments, the adapter is substantially or completely palindromic in nature. For example, in some embodiments, at least 30%, at least 35%, at least 40%, at least 45%, at least 50%, at least 55%, at least 60%, at least 65%, at least 70%, at least 75%, at least 80%, at least 85%, at least 90%, or at least 95% of the adapter may be palindromic. With a palindromic adapter, the adapter cannot be added in an incorrect orientation to the nucleic acid. Similarly, if an adapter is added to another adapter, the two adapters will form a complete restriction site that can be cleaved using a suitable restriction endonuclease, especially if the restriction site portions are also palindromic. However, in some cases, the adapter is not fully palindromic, and there may be "bubble" regions that are not palindromic. For example, identification sequences 72 and/or 74 within the adapter may be chosen to not be palindromic.

One non-limiting example of an adapter is the following sequence:

(SEQ ID NO: 1)
TTAA<u>GGGCTTTC</u>GTATCC<u>GGGGG</u>ACCTTAATTAAGGT<u>GGGGG</u>GGATAC<u>CT

TTCGGG</u>TTAA

It should be noted that this sequence is not fully palindromic, as certain regions (such as the underlined portions) are not palindromic. In this example, the two outer underlined regions may be used as identification sequences within the adapter. It should be noted that these regions are mirror images of each other, e.g., for ease of identification, rather than palindromes of each other (although this is not necessarily a requirement of the adapter). Other sequences (such as the repeating GGGGG portions in this particular example) may also be selected to be nonpalindromic, e.g., so that the adapter does not readily form stem-loop structures. In addition, the primer TAAGGTGGGGGGGATAC (SEQ ID NO: 2) may be used with this adapter.

The identification sequence may comprise any suitable number of nucleotides (for example, 4, 5, 6, 7, 8, 9, 10, 11, 12, 13, 14, 15, or more nucleotides). In some cases, a plurality of adapters is prepared, containing identical (or substantially similar) restriction sites but different identification sequences. The different adapters may all thus be of the same length, in some embodiments. Depending on the number of nucleotides chosen to be the identification sequence, a number of unique adapter sequences can be created. For example, if the identification sequence is 4 nucleotides long, then up to $4^4$ unique adapters may be created; if the identification sequence is 5 nucleotides long, then up to $4^5$ unique adapters may be created; etc. (e.g., up to $4^n$ unique sequences where n is the number of nucleotides in the identification sequence).

In some cases, the adapter may also contain a suitable primer sequence, e.g., such that the adapter may be recognized by an enzyme used in PCR ("Polymerase Chain Reaction"). Typically, the length of primer sequence is not more than about 30 nucleotides. Such a primer may be used, for example, to amplify the DNA (or RNA, in some cases) that the adapter is bound to.

A variety of techniques may be used to prepare the library of adapters. For example, microwell plates, containing wells containing the members of the library could be fabricated, e.g., using automated techniques, then encapsulated into droplets or other compartments. As another example, a randomized oligomer population could be encapsulated no more than one in a drop and amplified within each droplet or compartment. In some cases, a library of adapters may be present on a solid support. Examples include particles such as magnetic particles, hydrogel beads, agarose beads, or sepharose beads.

Any suitable ligase may be used to ligate the adapter to DNA or RNA. Many such ligases are commercially available, e.g., Epicentre®. In addition, enzymes such as End-It™ may be used, e.g., to repair DNA ends that were subjected to MNase degradation.

In some cases, the cell lysate is exposed to a solution containing adapters (e.g., with ligases) to cause the adapters to bind to the DNA. The solution may be contained within a droplet or other compartment. The action of the ligases may cause the adapters to be added randomly to the DNA. For example, an adapter may be ligated to one or both ends of a DNA strand, more than one adapter may be ligated to one end of a strand (e.g., ligated to each other), one or more adapters can be ligated to one or both ends of the DNA and to each other to produce a circular DNA fragment, and in some cases, adapters may be ligated directly to each other without any DNA in between. However, in a subsequent step, the DNA may be exposed to a restriction endonuclease that is able to cleave the adapters at a cleavage site. Doing so effectively causes the only half of the adapter to stay behind on the DNA (containing the identification sequence), while the rest of the adapters (and any other adapters that may have been connected to the first adapter) will be cleaved away. Accordingly, at the end of this step, at least some of the DNA will have an end labeled with a unique identification sequence at one or both ends, and thus, the DNA can be determined using the identification sequence, even if later mixed with DNA similarly processed but containing different identification sequences. Shorter fragments (e.g., the cleaved ends of the adapters, remains of adapters bound to each other that also been cleaved into small fragments, etc.) can be subsequently removed through regular DNA purification methods (size cut off), or left in solution but ignored. Thus, by tracking the different identification sequences, the genetic or epigenetic of cells can each be separately determined, e.g., potentially at a single cell level.

In one set of embodiments, the cell lysate (contained within droplets or other compartments) are fused or coalesced with other droplets containing adapters. In some cases, substantially each of the droplets or compartments contain unique adapters (i.e., the adapters may be substantially similar, but contain different identification sequences). Accordingly, the cell lysate of each droplet or compartment can be uniquely identified by determining the identification sequences.

Any suitable technique may be used to fuse a first droplet and a second droplet together to create a combined droplet. For example, the first and second droplets each be given opposite electric charges (i.e., positive and negative charges, not necessarily of the same magnitude), which may increase the electrical interaction of the two droplets such that fusion or coalescence of the droplets can occur due to their opposite electric charges, e.g., to produce the combined droplet. For instance, an electric field may be applied to the droplets, the droplets may be passed through a capacitor, a chemical reaction may cause the droplets to become charged, etc.

In another set of embodiments, the separate droplets may not necessarily be given opposite electric charges (and, in some cases, may not be given any electric charge), and the droplets may instead be fused through the use of dipoles induced in the fluidic droplets that causes the fluidic droplets to coalesce. The dipoles may be induced using an electric field which may be an AC field, a DC field, etc., and the electric field may be created, for instance, using one or more electrodes. The induced dipoles in the fluidic droplets may cause the fluidic droplets to become electrically attracted towards each other due to their local opposite charges, thus causing the droplets to fuse.

Still other examples of fusing or coalescing separate droplets to produce combined droplets are described in International Patent Application No. PCT/US2004/010903, filed Apr. 9, 2004, entitled "Formation and Control of Fluidic Species," by Link, et al., published as WO 2004/091763 on Oct. 28, 2004, and International Patent Application No. PCT/US2004/027912, filed Aug. 27, 2004, entitled "Electronic Control of Fluidic Species," by Link, et al., published as WO 2005/021151 on Mar. 10, 2005, each incorporated herein by reference in its entirety.

After ligation of the adapter, the various droplets or compartments containing DNA may be combined together in some aspects of the invention, e.g., to produce a common solution containing the DNA. Although the DNA may have arisen from different cells or compartments, due to the presence of the ligated adapters (e.g., containing unique identification sequences), the DNA is now distinguishable. The droplets may be combined by removing surfactant, removing the continuous fluid containing the droplets, or any other suitable technique.

The DNA may be processed or sequenced using any suitable technique, in accordance with certain aspects of the invention. For example, techniques such as Chromatin Immunoprecipitation ("ChIP"), ChIP-Sequencing, ChIP-on-chip, fluorescent in situ hybridization, methylation-sensitive restriction enzymes, DNA adenine methyltransferase identification (DamID), or bisulfite sequencing may be used to analyze the labeled DNA. Optionally, the DNA may be amplified, e.g., using PCR techniques known to those of ordinary skill in the art.

In one set of embodiments, some of the DNA may be analyzed or sequenced to determine a certain feature or characteristic. For example, in one set of embodiments, some of the DNA, still attached to nucleosomal structure, may be immunoprecipitated by exposing the fragments to an antibody, for example, a histone-recognizing antibody such as H3-lysine-4-methyl, or the naked DNA to a methylcytosine antibody, or a hydroxymethylcytosine antibody. Thus, for example, DNA having a certain feature (e.g., methylated histones or deacylated histones) may be removed and analyzed or sequenced. Other examples of histone modifications that may be studied include acetylation, methylation, ubiquitylation, phosphorylation and sumoylation.

In some cases, the DNA that is sequenced may be aligned with a genome (e.g., a known genome, such as a human genome) to determine locations of the DNA within the genome (e.g., of a particular cell) that exhibit such features (e.g., methylated histones or deacylated histones). Thus, for example, certain nucleosomes within the genome may be identified as exhibiting such features. An example of such a study is discussed below in Example 1.

In other embodiments, RNA molecules, e.g., from individual cells, could be "barcoded" or otherwise ligated with an identification sequence in droplets (or other compartments) using single stranded indexed adaptors. The adaptors may be coupled to the RNA molecules, for example, by direct ligation, by poly-T or random primer-based reverse transcription methods, or by other methods known to those of ordinary skill in the art. In some embodiments, selected RNA sequences could be interrogated by introducing a collection of single-stranded adaptors each comprising a barcode or other identification sequence (e.g., indexed to a single cell) and known sequences complementary to the RNA species of interest, followed by reverse transcription in single-cell-containing droplets. Template switching may be used in some embodiments. Accordingly, it should be understood that in the embodiments and examples discussed herein using DNA, this is by way of example only, and that in other embodiments, RNA could be used instead of and/or in addition to DNA.

A variety of materials and methods, according to certain aspects of the invention, can be used to produce fluidic systems and microfluidic systems such as those described herein. In some cases, the various materials selected lend themselves to various methods. For example, various components of the invention can be formed from solid materials, in which the channels can be formed via micromachining, film deposition processes such as spin coating and chemical vapor deposition, laser fabrication, photolithographic techniques, etching methods including wet chemical or plasma processes, and the like. See, for example, *Scientific American*, 248:44-55, 1983 (Angell, et al). In one embodiment, at least a portion of the fluidic system is formed of silicon by etching features in a silicon chip. Technologies for precise and efficient fabrication of various fluidic systems and devices of the invention from silicon are known. In another embodiment, various components of the systems and devices of the invention can be formed of a polymer, for example, an elastomeric polymer such as polydimethylsiloxane ("PDMS"), polytetrafluoroethylene ("PTFE" or Teflon®), or the like.

Different components can be fabricated of the same or different materials. For example, a base portion including a bottom wall and side walls can be fabricated from an opaque material such as silicon or PDMS, and a top portion can be fabricated from a transparent or at least partially transparent material, such as glass or a transparent polymer, for observation and/or control of the fluidic process. Components can be coated so as to expose a desired chemical functionality to fluids that contact interior channel walls, where the base supporting material does not have a precise, desired functionality. For example, components can be fabricated as illustrated, with interior channel walls coated with another material. Material used to fabricate various components of the systems and devices of the invention, e.g., materials used to coat interior walls of fluid channels, may desirably be selected from among those materials that will not adversely affect or be affected by fluid flowing through the fluidic system, e.g., material(s) that is chemically inert in the presence of fluids to be used within the device.

In one embodiment, various components of the invention are fabricated from polymeric and/or flexible and/or elastomeric materials, and can be conveniently formed of a hardenable fluid, facilitating fabrication via molding (e.g. replica molding, injection molding, cast molding, etc.). The hardenable fluid can be essentially any fluid that can be induced to solidify, or that spontaneously solidifies, into a solid capable of containing and/or transporting fluids contemplated for use in and with the fluidic network. In one embodiment, the hardenable fluid comprises a polymeric liquid or a liquid polymeric precursor (i.e. a "prepolymer"). Suitable polymeric liquids can include, for example, thermoplastic polymers, thermoset polymers, or mixture of such polymers heated above their melting point. As another example, a suitable polymeric liquid may include a solution of one or more polymers in a suitable solvent, which solution forms a solid polymeric material upon removal of the solvent, for example, by evaporation. Such polymeric materials, which can be solidified from, for example, a melt state or by solvent evaporation, are well known to those of ordinary skill in the art. A variety of polymeric materials, many of which are elastomeric, are suitable, and are also suitable for forming molds or mold masters, for embodiments where one or both of the mold masters is composed of an elastomeric material. A non-limiting list of examples of such polymers includes polymers of the general classes of silicone polymers, epoxy polymers, and acrylate polymers. Epoxy polymers are characterized by the presence of a three-membered cyclic ether group commonly referred to as an epoxy group, 1,2-epoxide, or oxirane. For example, diglycidyl ethers of bisphenol A can be used, in addition to compounds based on aromatic amine, triazine, and cycloaliphatic backbones. Another example includes the well-known Novolac polymers. Non-limiting examples of silicone elastomers suitable for use according to the invention include those formed from precursors including the chlorosilanes such as methylchlorosilanes, ethylchlorosilanes, phenylchlorosilanes, etc.

Silicone polymers are preferred in one set of embodiments, for example, the silicone elastomer polydimethylsiloxane. Non-limiting examples of PDMS polymers include those sold under the trademark Sylgard by Dow Chemical Co., Midland, Mich., and particularly Sylgard 182, Sylgard 184, and Sylgard 186. Silicone polymers including PDMS have several beneficial properties simplifying fabrication of the microfluidic structures of the invention. For instance, such materials are inexpensive, readily available, and can be solidified from a prepolymeric liquid via curing with heat. For example, PDMSs are typically curable by exposure of the prepolymeric liquid to temperatures of about, for example, about 65° C. to about 75° C. for exposure times of, for example, about an hour. Also, silicone polymers, such as PDMS, can be elastomeric, and thus may be useful for forming very small features with relatively high aspect ratios, necessary in certain embodiments of the invention. Flexible (e.g., elastomeric) molds or masters can be advantageous in this regard.

One advantage of forming structures such as microfluidic structures of the invention from silicone polymers, such as PDMS, is the ability of such polymers to be oxidized, for example by exposure to an oxygen-containing plasma such as an air plasma, so that the oxidized structures contain, at their surface, chemical groups capable of cross-linking to other oxidized silicone polymer surfaces or to the oxidized surfaces of a variety of other polymeric and non-polymeric materials. Thus, components can be fabricated and then oxidized and essentially irreversibly sealed to other silicone polymer surfaces, or to the surfaces of other substrates reactive with the oxidized silicone polymer surfaces, without the need for separate adhesives or other sealing means. In most cases, sealing can be completed simply by contacting an oxidized silicone surface to another surface without the need to apply auxiliary pressure to form the seal. That is, the pre-oxidized silicone surface acts as a contact adhesive against suitable mating surfaces. Specifically, in addition to being irreversibly sealable to itself, oxidized silicone such as oxidized PDMS can also be sealed irreversibly to a range of oxidized materials other than itself including, for example, glass, silicon, silicon oxide, quartz, silicon nitride, polyethylene, polystyrene, glassy carbon, and epoxy polymers, which have been oxidized in a similar fashion to the PDMS surface (for example, via exposure to an oxygen-containing plasma). Oxidation and sealing methods useful in the context of the present invention, as well as overall molding techniques, are described in the art, for example, in an article entitled "Rapid Prototyping of Microfluidic Systems and Polydimethylsiloxane," *Anal. Chem.*, 70:474-480, 1998 (Duffy, et al.), incorporated herein by reference.

In some embodiments, certain microfluidic structures of the invention (or interior, fluid-contacting surfaces) may be formed from certain oxidized silicone polymers. Such surfaces may be more hydrophilic than the surface of an elastomeric polymer. Such hydrophilic channel surfaces can thus be more easily filled and wetted with aqueous solutions.

In one embodiment, a bottom wall of a microfluidic device of the invention is formed of a material different from one or more side walls or a top wall, or other components. For example, the interior surface of a bottom wall can comprise the surface of a silicon wafer or microchip, or other substrate. Other components can, as described above, be sealed to such alternative substrates. Where it is desired to seal a component comprising a silicone polymer (e.g.

PDMS) to a substrate (bottom wall) of different material, the substrate may be selected from the group of materials to which oxidized silicone polymer is able to irreversibly seal (e.g., glass, silicon, silicon oxide, quartz, silicon nitride, polyethylene, polystyrene, epoxy polymers, and glassy carbon surfaces which have been oxidized). Alternatively, other sealing techniques can be used, as would be apparent to those of ordinary skill in the art, including, but not limited to, the use of separate adhesives, thermal bonding, solvent bonding, ultrasonic welding, etc.

As mentioned, in some, but not all embodiments, the systems and methods described herein may include one or more microfluidic components, for example, one or more microfluidic channels. The "cross-sectional dimension" of a microfluidic channel is measured perpendicular to the direction of fluid flow within the channel. Thus, some or all of the microfluidic channels may have a largest cross-sectional dimension less than 2 mm, and in certain cases, less than 1 mm. In one set of embodiments, the maximum cross-sectional dimension of a microfluidic channel is less than about 500 micrometers, less than about 300 micrometers, less than about 200 micrometers, less than about 100 micrometers, less than about 50 micrometers, less than about 30 micrometers, less than about 10 micrometers, less than about 5 micrometers, less than about 3 micrometers, or less than about 1 micrometer. In certain embodiments, the microfluidic channels may be formed in part by a single component (e.g. an etched substrate or molded unit). Of course, larger channels, tubes, chambers, reservoirs, etc. can also be used to store fluids and/or deliver fluids to various components or systems in other embodiments of the invention.

A microfluidic channel can have any cross-sectional shape (circular, oval, triangular, irregular, square or rectangular, or the like) and can be covered or uncovered. In embodiments where it is completely covered, at least one portion of the channel can have a cross-section that is completely enclosed, or the entire channel may be completely enclosed along its entire length with the exception of its inlet(s) and/or outlet(s). A channel may also have an aspect ratio (length to average cross sectional dimension) of at least 2:1, more typically at least 3:1, 5:1, 10:1, 15:1, 20:1, or more.

In some embodiments, at least a portion of one or more of the channels may be hydrophobic, or treated to render at least a portion hydrophobic. For example, one non-limiting method for making a channel surface hydrophobic comprises contacting the channel surface with an agent that confers hydrophobicity to the channel surface. For example, in some embodiments, a channel surface may be contacted (e.g., flushed) with Aquapel® (a commercial auto glass treatment) (PPG Industries, Pittsburgh, Pa.). In some cases, a channel surface contacted with an agent that confers hydrophobicity may be subsequently purged with air. In some embodiments, the channel may be heated (e.g., baked) to evaporate solvent that contains the agent that confers hydrophobicity.

Thus, in some aspects of the invention, a surface of a microfluidic channel may be modified, e.g., by coating a sol-gel onto at least a portion of a microfluidic channel. As an example, the sol-gel coating may be made more hydrophobic by incorporating a hydrophobic polymer in the sol-gel. For instance, the sol-gel may contain one or more silanes, for example, a fluorosilane (i.e., a silane containing at least one fluorine atom) such as heptadecafluorosilane, or other silanes such as methyltriethoxy silane (MTES) or a silane containing one or more lipid chains, such as octadecylsilane or other $CH_3(CH_2)_n$-silanes, where n can be any suitable integer. For instance, n may be greater than 1, 5, or 10, and less than about 20, 25, or 30. The silanes may also optionally include other groups, such as alkoxide groups, for instance, octadecyltrimethoxysilane. In general, most silanes can be used in the sol-gel, with the particular silane being chosen on the basis of desired properties such as hydrophobicity. Other silanes (e.g., having shorter or longer chain lengths) may also be chosen in other embodiments of the invention, depending on factors such as the relative hydrophobicity or hydrophilicity desired. In some cases, the silanes may contain other groups, for example, groups such as amines, which would make the sol-gel more hydrophilic. Non-limiting examples include diamine silane, triamine silane, or N-[3-(trimethoxysilyl)propyl] ethylene diamine silane. The silanes may be reacted to form oligomers or polymers within the sol-gel, and the degree of polymerization (e.g., the lengths of the oligomers or polymers) may be controlled by controlling the reaction conditions, for example by controlling the temperature, amount of acid present, or the like. In some cases, more than one silane may be present in the sol-gel. For instance, the sol-gel may include fluorosilanes to cause the resulting sol-gel to exhibit greater hydrophobicity, and/or other silanes (or other compounds) that facilitate the production of polymers. In some cases, materials able to produce $SiO_2$ compounds to facilitate polymerization may be present, for example, TEOS (tetraethyl orthosilicate). It should be understood that the sol-gel is not limited to containing only silanes, and other materials may be present in addition to, or in place of, the silanes. For instance, the coating may include one or more metal oxides, such as $SiO_2$, vanadia ($V_2O_5$), titania ($TiO_2$), and/or alumina ($Al_2O_3$).

In some instances, the microfluidic channel is constructed from a material suitable to receive the sol-gel, for example, glass, metal oxides, or polymers such as polydimethylsiloxane (PDMS) and other siloxane polymers. For example, in some cases, the microfluidic channel may be one in which contains silicon atoms, and in certain instances, the microfluidic channel may be chosen such that it contains silanol (Si—OH) groups, or can be modified to have silanol groups. For instance, the microfluidic channel may be exposed to an oxygen plasma, an oxidant, or a strong acid cause the formation of silanol groups on the microfluidic channel.

If compartments are used, the compartments may be wells of a microwell plate (e.g., a 96-well, a 384-well, a 1536-well, a 3456-well microwell plate, etc.). In yet other embodiments, the compartments may be individual tubes or containers, test tubes, microfuge tubes, glass vials, bottles, petri dishes, wells of a plate, or the like. In some cases, the compartments may have relatively small volumes (e.g., less than about 1 microliter, less than about 300 nl, less than about 100 nl, less than about 30 nl, less than about 10 nl, less than about 3 nl, less than about 1 nl, etc.). In some cases, the compartments may be individually accessible.

The following documents are incorporated herein by reference in their entireties: International Patent Application No. PCT/US2004/010903, filed Apr. 9, 2004, entitled "Formation and Control of Fluidic Species," by Link, et al., published as WO 2004/091763 on Oct. 28, 2004; International Patent Application No. PCT/US2003/020542, filed Jun. 30, 2003, entitled "Method and Apparatus for Fluid Dispersion," by Stone, et al., published as WO 2004/002627 on Jan. 8, 2004; International Patent Application No. PCT/US2006/007772, filed Mar. 3, 2006, entitled "Method and Apparatus for Forming Multiple Emulsions," by Weitz, et al., published as WO 2006/096571 on Sep. 14, 2006; International Patent Application No. PCT/US2004/027912, filed Aug. 27, 2004, entitled "Electronic Control of Fluidic Species," by Link, et al., published as WO 2005/021151 on Mar. 10, 2005; International Patent Application No. PCT/US2007/002063, filed Jan. 24, 2007, entitled "Fluidic Droplet Coalescence," by Ahn, et al., published as WO 2007/089541 on Aug. 9, 2007; International Patent Application No. PCT/US2008/013912, filed Dec. 19, 2008, entitled "Systems and Methods for Nucleic Acid Sequencing," by Weitz, et al., published as WO 2009/085215 on Jul. 9, 2009; and International Patent Application No. PCT/US2008/008563, filed Jul. 11, 2008, entitled "Droplet-Based Selection," by Weitz, et al., published as WO 2009/011808 on Jan. 22, 2009. Also incorporated by reference in its entirety is U.S. Provisional Patent Application Ser. No. 61/634,744, filed Mar. 5, 2012, entitled "Systems and Methods for Epigenetic Sequencing," by Rotem, et al.

The following examples are intended to illustrate certain embodiments of the present invention, but do not exemplify the full scope of the invention.

Example 1

This example illustrates certain systems and methods for profiling epigenomes of single cells within populations using droplet based microfluidics.

All cell types in the human contain essentially identical genomes (i.e., the DNA sequence). However they vary in terms of how the DNA is organized by chromatin, a higher order structure of protein, DNA and RNA. Chromatin structure plays an important role in regulating genome function and in particular its varied structure across cell types helps ensure that the correct genes are expressed in the correct cell types. Chromatin structure is regulated by histone modifications and DNA methylation. Thus, genomewide maps of histone modifications or DNA methylation in a given cell type are a valuable research tool. These maps are collectively referred to as epigenomic profiles or "epigenomes." In addition to their value for understanding normal development, epigenomic profiles have clinical relevance as they can identify defects in genome regulation in cancer or other diseases, propose therapeutic strategies or serve as diagnostic or early detection biomarkers.

Current methods for profiling epigenomes require thousands of cells. For example, histone modifications can be mapped by immunoprecipitating chromatin with antibodies to a modified histone and then sequencing the DNA (ChIP-seq). However, this method requires ~100,000 cells or more. Furthermore, the analysis is carried out on the entire population and is blind to differences among cells. Approaches capable of profiling epigenomes in single cells are important for understanding the principles of chromatin and genome regulation. Moreover, such approaches could have many clinical applications in cancer biology, immunology, neuroscience or other fields in which subject tissues are complex, heterogeneous and/or limited in size. For example, tumors represent heterogeneous mixtures of cells that may be driven by sub-populations of cancer stem cells. Single cell epigenomic profiling methods could improve understanding of critical epigenomic changes in cancer stem cells. They might also enable early detection or surveillance of disease.

This example describes an epigenomic profiling method that can be used to map histone modifications in hundreds, thousands or more individual cells in a population. This example uses microfluidic devices to capture single cells in single droplets. The cells are then lysed and the genome is fragmented by enzymatic digestion in the droplets. Finally, DNA oligonucleotides with unique "barcodes" or identification sequences are added to each droplet and ligated to the fragmented genomic DNA sequences, thus providing a unique identifier for each individual cell. The materials now includes DNA fragments wrapped around histones and "bar coded" according to the cell from which they originated. The materials can now be combined (e.g., "combined and indexed chromatin matter") and subjected to epigenomic profiling.

In some embodiments, profiling can be performed by using chromatin immunoprecipitation using an antibody against a modified histone (e.g., histone H3 lysine 4 trimethyl). After "pull-down" or separation of nucleosomes associated with this modified histone form (e.g., on a substrate), the DNA is isolated and bar-coded fragments are selectively introduced into a sequencing library. The DNA is then sequenced, for example, using next-generation sequencing instruments (e.g., Illumina HiSeq).

After sequencing, data may be processed in the following succession: (i) each read is assigned to an original cell based on its bar code; (ii) each read is aligned to the genome based on the sequence attached to the bar code; (iii) genomewide profiles are generated for each cell, based on the union of reads with the same bar code—specifically, the profiles reflect the density of reads as a function of genomic position. Furthermore, (iv) clustering algorithms can be applied to the individual profiles and used to identify dominant patterns characteristic of different cellular states in a heterogeneous population.

As a specific example, using a microfluidic device, cells may be encapsulated in drops at a density of at most one cell per drop. The cells are lysed and chromatin is fragmented by MNase enzymatic digestion into its single units, called nucleosomes (special buffer was optimized, including Triton, MNase and $CaCl_2$ to complement MNase requirements). Each nucleosome included a segment of DNA wound around a histone protein core. By a process of droplet fusion, each droplet containing cells is fused with a droplet containing a cocktail of enzymes, including EndIt (Epicentre: repairs DNA ends that were subjected to MNase digestion), ligase (Epicentre), modified buffer including EGTA that stops the MNase digestion, and double-stranded, barcoded oligonucleotide adapters.

The oligonucleotide adapter comprised a barcode that is unique, specific to each droplet (or individual cell). It also contains a universal PCR primer sequence and a restriction site (i.e., the oligonucelotides vary in terms of their barcodes, but are constant in terms of the primer sequence and restriction site). The enzyme cocktail effectively ligates barcoded adapters to the ends of the DNA fragments in the droplet. Thus, after barcoding, each piece includes a fragment of genome flanked by barcoded adapters and wrapped around histones. Before breaking the droplets and merging them to form one aqueous volume, dilution buffer is supplemented, including both EGTA and EDTA in concentrations that will stop any enzymatic reaction and maintain detergent levels.

Since these complexes are "bar-coded" with identification sequences by their cell of origin, they may now be combined for epigenomic profiling. Specifically, the droplets are pooled together and broken down to form one aqueous volume. This combined and indexed chromatin matter is then subjected to immunoprecipitation or "ChIP" using an antibody, e.g., an antibody against a histone modification (e.g., H3 lysine 4 trimethyl or H3 lysine 4 methyl). This enriches for fragments associated with histones having this modification. The enriched DNA is then isolated using any suitable technique.

Fragments within the enriched DNA sample that have "bar-coded" adapters attached can be selected by amplification followed by restriction, using the universal primer and the restriction sites on the adapters. The restriction event leaves an end that is compatible with a next round of ligation to sequencing adapters. The result is a sequencing library that contains "bar-coded" sequences from the epigenomic enrichment assay. The "bar-codes" may serve as indexes that allow DNA fragments to be assigned to individual single cells. The fragments can also be aligned to a genome. For example, a computational pipeline design including demultiplexing of the sequenced DNA can be aligned to a genome using known techniques such as a Bowtie algorithm, a Peak-calling using Scripture algorithm, and/or clustering to elucidate different population profiles.

The cells may be encapsulated in drops at rates of thousands per second, or millions per hour. To prepare a library of unique barcodes, the contents of a micro-titer well plate containing oligonucleotides (e.g., an oligonucleotide library) may be sequenced. In some cases, a randomized oligomer population can be encapsulated at no more than one in a drop and amplified inside each drop to create a homogenized oligomer drop catalog.

Example 2

This example illustrates various techniques useful for epigenetic sequencing in accordance with certain embodiments of the invention Cell culture. K562 erythrocytic leukaemia cells (ATCC CCL-243) were grown according to standard protocols in RPMI 1640 media (Invitrogen, 22400105) supplemented with 10% fetal bovine serum (FBS, Atlas Biologicals, F-0500-A) and 10% penicillin/streptomycin (Invitrogen, 15140122).

Cell lysis and chromatin digestion in droplets. Using a microfluidic device, cells were encapsulated in droplets at a density of at most one cell per droplet.

The cells were lysed and chromatin was fragmented in 1% Triton, 0.1% sodium deoxycholate, 50 mM Tris-HCl pH 7.5, 150 mM NaCl supplemented with 10 units/ml of MNase (Thermo scientific, 88216), 1 mM $CaCl_2$ and EDTA-free protease inhibitor (Roche, 13015000). The cells were incubated for 10 min at 4° C., 15 min at 37° C., and put back at 4° C. until the next step.

Adapter ligation in droplets. Each nucleosome was formed from a segment of DNA wound around a histone protein core. By a process of droplet fusion, the droplets (typically containing a single cell) was fused with a droplet contains unique barcoded adaptor in a final concentration of 500 micromolar. Additional buffer was pico-injected into the fused droplets at the same time. This buffer had a total volume of 104 microliters and contained 8 microliters End-It™ (Epicentre, ER81050) that repairs DNA ends that were subjected to MNase digestion, 20 microliters End-It™ buffer, 8 Fast link ligase (Epicentre, LK6201H), 20 microliters fast link ligation buffer, 20 microliters dNTPs, 12 microliters from 10 mM ATP, and 8 microliters EGTA to a final concentration of 40 mM that stopped the MNase digestion.

The cells may be encapsulated in droplets at rates of thousands per second, or millions per hour. To prepare a library of unique barcodes, the contents of a micro-titer well plate containing the oligo-library could be encapsulated in droplets. Alternatively, a randomized oligomer population could be encapsulated no more than one in a droplet and amplified inside each droplet to create a homogenized oligomer droplet catalog.

Adapter design. The oligomer adapters used in this example comprised an 8-mer identification sequence (or "barcode") that was unique to each droplet (individual cell). The adapters also contained a universal PCR primer sequence (forward: ACACGCAGTATCCCTTCG (SEQ ID NO: 3), reverse: ACTGCGTGTATCCGACTC (SEQ ID NO: 4)) and a restriction site for BciVI (NEB, R0596S) that cuts at a 3' overhang. Thus, the oligomers varied in terms of their identification sequences, but were constant in terms of the primer sequence and restriction site. The enzyme cocktail effectively ligated blunt ended barcoded adaptors to the ends of the repaired DNA fragments in the droplet. Thus, after ligating the adapter, the nucleic acids typically included a fragment of genome flanked by barcoded adaptors and wrapped about histones.

Breaking droplets. Since the nucleic acids were uniquely labeled with the adapters by their cell of origin, they could subsequently be combined for epigenomic profiling. The droplets were pooled together and broken into one aqueous volume. Before breaking the droplets into one aqueous volume, dilution buffer (50 mM Tris-HCl pH 7.5, 150 mM NaCl, 1% Triton, 20 mM EGTA, and 20 mM EDTA) was added. The concentrations of EGTA, EDTA, and detergent were thus maintained (i.e., at 20 mM, 10 mM, and 1%, respectively). 1H,1H,2H,2H-perfluoro-1-octanol, 97% (Sigma, 370533-25G) was used to break the droplets.

Chromatin imunoprecipitation. Next 5 to 10 micrograms of H3K4me3 antibody (Millipore, 17-614) were pre-bound by incubating with a mix of Protein-A and Protein-G Dynabeads (Invitrogen, 100-02D and 100-07D, respectively) in blocking buffer (PBS supplemented with 0.5% TWEEN and 0.5% BSA) for 2 hours. Washed beads were added to the chromatin lysate (aqueous phase of broken droplets) for overnight incubation. The samples were washed 6 times with RIPA buffer, twice with RIPA buffer supplemented with 500 mM NaCl, twice with LiCl buffer (10 mM TE, 250 mM LiCl, 0.5% NP-40, 0.5% DOC), twice with TE (10 mM Tris-HCl pH 8.0, 1 mM EDTA), and then eluted with 0.5% SDS, 300 mM NaCl, 5 mM EDTA, 10 mM Tris-HCl pH 8.0 at 65° C. The eluant was incubated in 65° C. for 1 hour, then treated sequentially with RNaseA (Roche, 11119915001) for 30 min and Proteinase K (NEB, P8102S) for two hours. The DNA was purified using Agencourt AMPure XP beads (Beckmangenomics, A63881).

Sequencing library preparation. Fragments within the enriched DNA sample that had ligated adapters were selected by amplification followed by restriction using the universal primer and the restriction sites on the adapters as described herein. The restriction event leaves a 3' A overhang that was compatible with a next round of Ilumina adapter ligation. The result was a sequencing library that was enriched with nucleic acids from the epigenomic enrichment assay. The identification sequences or "barcodes" within the nucleic acids then served as indexes that allowed the DNA fragments to be assigned to individual single cells.

Computational pipeline. The first step included de-multiplexing of the sequenced reads, first, according to the Ilumina indexes and then for the 8-mer indexes implemented on each read and hold cell origin information for each fragment. Next, the Bowtie algorithm was used to align the reads to the genome and a peak-caller (Scripture algorithm) to find regions with significant signal to noise ratios. Finally, panning was performed by clustering single cell epigenome profiles to elucidate the heterogeneity in cell population, detect different cell types in mixed population, and/or extract other information from the cells.

Example 3

This is an example of profiling cellular populations at the single cell level with drop-based microfluidics. Populations of cells have substantial heterogeneity that is important for their function and understanding. This variability is reflected in cell to cell variations of epigenetic features such as DNA methylation, chromatin organization, mRNA levels, and protein expression. When characterizing a pool of cells by conventional methods, these variations are quickly averaged and cannot be detected. To detect these variations, populations can be sorted by phenotype prior to characterization but ideally, cells could be characterized one-by-one. The problem of averaging over multiple cells is exacerbated when a small number of cells differ from the majority of the population. An example is the case of rare variants that are increasingly realized to underlie tumor biology and therapeutic resistance. Since the phenotype of these rare cells is yet to be discovered, presorting them is not an option. Thus, a method for characterizing multiple single cells at very high throughput is needed for understanding the behavior and function of biological systems ranging from developing blood cells to human tumors. Accordingly, this example illustrates scalable and flexible microfluidics methodology capable of profiling chromatin state and RNA expression in thousands of single cells, and thereby capturing the nature of population heterogeneity at unprecedented scale.

Characterizing the genetic and epigenetic states of single cells is a challenge because the effective concentration of the contents of a single cell is a million times smaller than that of typical samples that pool many cells, and hence the rate of reactions becomes impractically slow. In some cases, the content of the cell may be amplified prior to its characterization, as was previously used to measure single cell genetic variations or single cell RNA expression levels. However, amplifying the contents of single cells in wells is time consuming, expensive and thus not scalable to large numbers of cells; moreover, this solution is not relevant for assays involving proteins, which are denatured during amplification. Instead, this example restores the effective concentration in single cell assays by drastically decreasing the reaction volume using drop-based microfluidics.

Droplet-based microfluidics use drops of water immersed in an inert carrier fluid as minute reaction vessels that can be precisely controlled by microfluidic devices. As an example, the droplets may be roughly 10 micrometers in diameter, each containing about 1 pL of fluid surrounded by a surfactant that both stabilizes the droplet to prevent coalescence with other droplets, and protects its interface to prevent loss of reagents through surface adsorption. The reagents within the droplets never touch the walls of the microfluidic device and fluidic control may be achieved with the inert carrier fluid, totally independent of the droplets. The droplets can be formed, refilled, thermo-cycled, merged, split, sorted, etc. at rates of up to millions per hour with exquisite control over individual droplets. Thus, droplets can be used to compartmentalize millions of single cells per hour at high concentrations, allowing measurements of millions of single cells.

In these examples, a flexible platform for high through profiling of single cells is demonstrated. These examples thus show a general method that combines droplet-based microfluidics with genomics and DNA barcoding to profile genetic and epigenetic features of single cells. To analyze diverse populations, cells are encapsulated at about one per droplet, and then each droplet is fused with another droplet containing billions of copies of a unique barcode used to tag the contents of the cell, e.g., contained within an adaptor. After tagging each cell, the droplets are merged and downstream assays can be performed on the mix of barcoded cellular information before being sequenced. Upon sequencing, the cell of origin for each fragment can be identified by reading the barcode. The platform is compatible with both DNA and RNA, uses ligation or hybridization to attach the barcodes and can be scaled up to a large number of cells.

This general method can be used, for example, to study epigenetic heterogeneity. Gene regulation in eukaryotes relies on the functional packaging of DNA into chromatin, a higher-order structure composed of DNA, RNA, histones and associated proteins. Chromatin structure and function is regulated by post-translational modifications of the histones, including acetylation, methylation and ubiquitinylation. Histone modifications (HM) can be mapped genome-wide, revealing type-specific regulation states of cells that reflect lineage-specific gene expression, developmental programs or disease processes. Given the central role of HM in stem and cancer cells, it is likely that epigenetic states differ between tumor cells and underlie their functional heterogeneity. To map histone modifications across the genome, antibodies are used to bind to specific modification of the chromatin complex units, or nucleosomes, and then the bound DNA is sequenced in a protocol that is known as Chromatin Immuno-Precipitation sequencing (ChIP-Seq). However, mapping HM in single cells is not currently possible in other systems due to a low signal to noise ratio when performing ChIP on genomic material from less than 10,000 cells. These limitations can be overcome, for example, by uniquely barcoding the DNA of multiple cells and then performing ChIP-Seq on a pool rather than on a single cell. Thus, the high signal to noise ratio typical of ChIP is maintained and single cell information is restored by reading the barcodes.

Figure 5A:
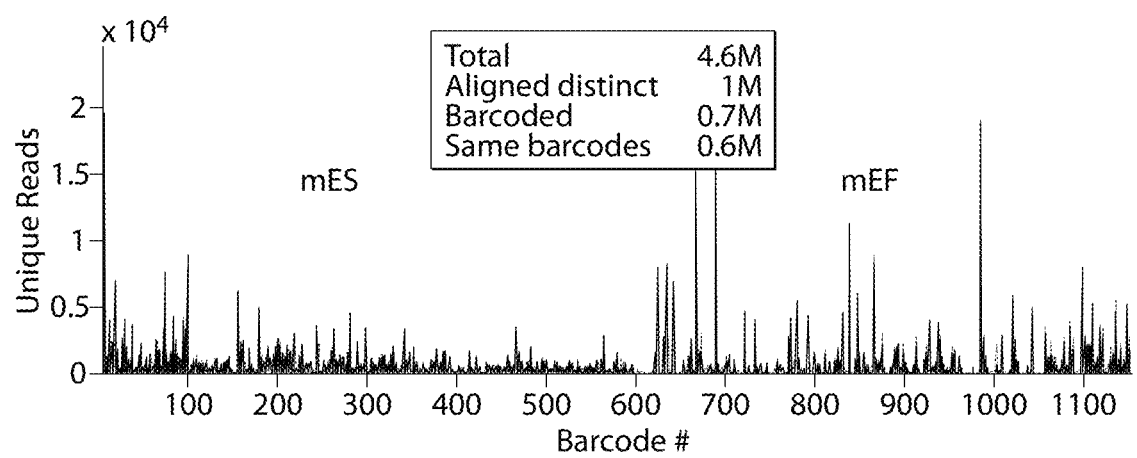
FIGS. 5A-5D illustrate unique barcodes within a population of cells, in yet another embodiment of the invention.

To perform ChIP-Seq on single cells, cells are encapsulated one in a drop together with lysis buffer and Micrococcal Nuclease enzyme (MNase) that digests inter-nucleosomal DNA. After digestion, each droplet containing fragmentized nucleosomes from a single cell is merged with a drop containing billions of copies of a unique DNA adapter and a ligation buffer as shown in FIG. 4. The merging transpires by applying an electric field through an electrode positioned within the device. To allow adequate sequencing coverage for the information obtained from the barcoded cells, only 100 merged droplets are collected per ChIP-Seq experiment. To ensure that each cell is tagged with a unique barcode, the barcode library contains at least 10 times more unique barcodes than the number of cells collected. Thus when collecting 100 cells, a library containing 1152 different barcodes is used, ensuring that the probability of barcoding two different cells with the same barcode is lower than 5%. Barcoded nucleosomes can be merged with additional non-barcoded nucleosomes used as a biological buffer to ensure high signal to noise ratios during the Immuno-Precipitation step. To enrich for barcoded nucleosomal fragments, the adapters may be designed with additional DNA sequences that are used as specific priming regions for amplification and as restriction sites for selection during the preparation of the library for Illumina sequencing. Thus, although initially the barcoded fragments make a negligible fraction of the DNA in the sample, the majority of sequenced reads are barcoded on both ends, as shown in FIG. 5A.

FIG. 4 shows microfluidics of a single cell ChIP-seq. FIG. 4A shows cells are encapsulated in drops together with lysis buffer and digestive enzyme. FIG. 4B shows that, after incubation, droplets are re-injected into another microfluidic device where they are fused with drops containing barcodes. FIG. 4C is an image of single cells being encapsulated in a microfluidic droplet maker. FIG. 4D shows droplets containing barcodes are fused with drops containing cell lysate. Scale bars are 100 micrometers.

To demonstrate that the epigenetic profiles of single cells could be measured, two distinct murine cell lines, mES and mEF, were encapsulated. Each cell line was separately tagged with different barcodes and then 50 merged drops from each cell line were collected and pooled together to undergo H3K4me3 ChIP-Seq. Thus, the cell type of each barcoded fragment was known a priori and could be compared to the separation obtained from analyzing the sequenced data. Although only 50 barcodes from each cell type are expected to be found in the sequenced data, all barcodes were present when analyzing the data, as shown in FIG. 5A. This is believed to be a result of cross-contamination between droplets that may occur during droplet merging due to electro-wetting of the microfluidic channel near the electrodes that were used to merge the droplets. Thus, to analyze our cellular information, barcodes that were used to tag cells were identified as those possessing the largest number of DNA fragments in the sample.

Figure 5B:
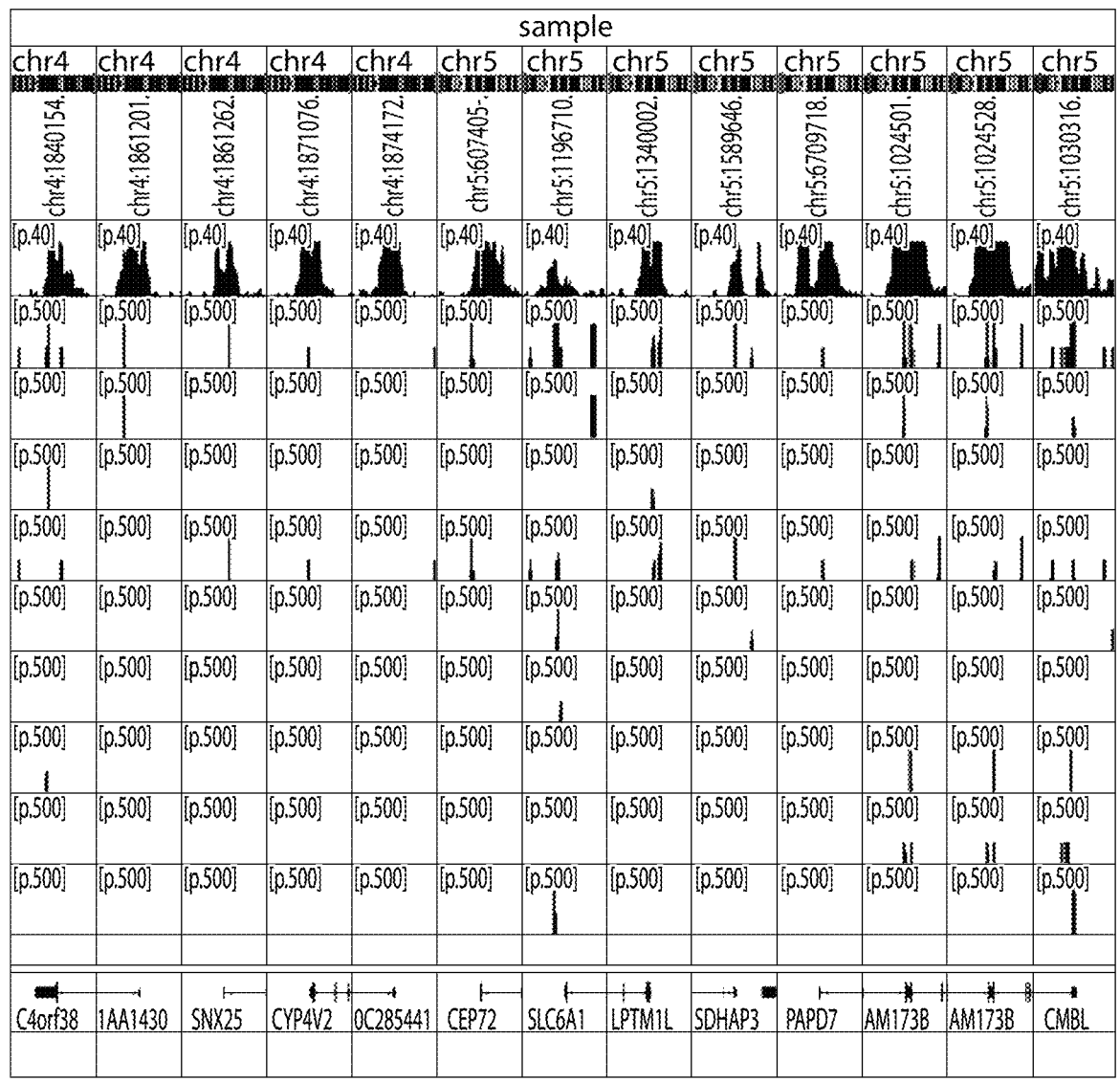
Figure 5C:
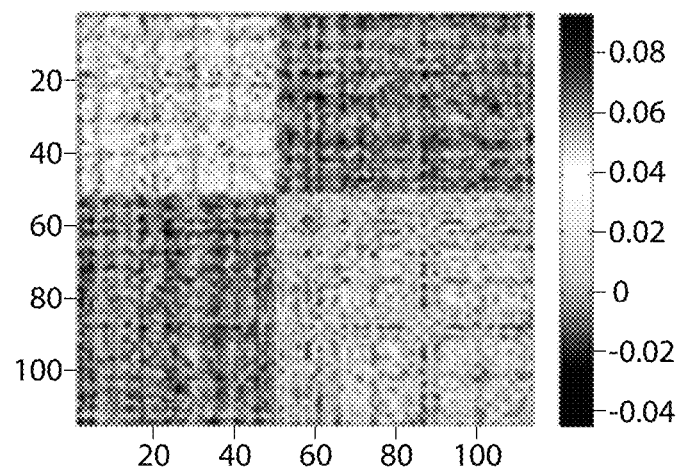
Figure 5D:
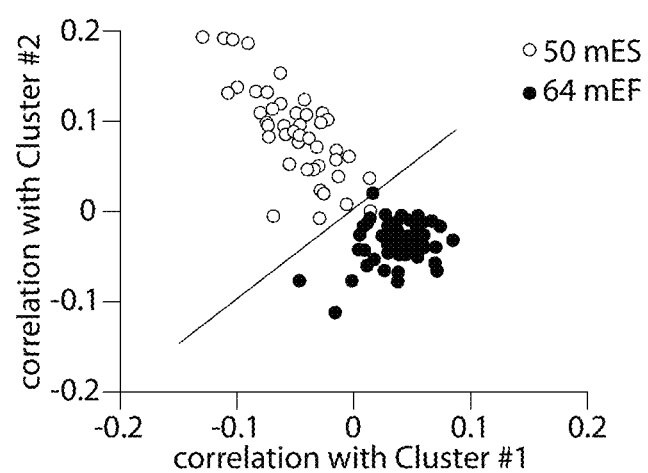

After aligning and filtering the reads, each of the chosen barcodes typically tagged 2-5,000 distinct DNA fragments from each single cell, representing a sparse binary vector spanning the murine genome with enrichment for positive entries in genomic regions that were wrapped around H3K4me3 marked nucleosomes. The complete set of chosen barcodes was represented as a sparse binary matrix, in which only 15,000 out of the 1 million genomic bins have reads from more than one cell and can therefore be used to compare between them. Despite the sparseness of the data, when aggregating all mES cells and all mEF cells the known profile measured in many cells in bulk was restored as shown in FIG. 5B; moreover, it was possible to separate the two types of cells from each other in an unsupervised way based on the correlations between the vectors of the different cells, as shown in FIGS. 5C and 5D. All but one barcode, each representing the data of a single cell, were successfully classified as originating from either mES or mEF cell lines demonstrating that biologically relevant data could be measured from single cells using ChIP-Seq.

Thus, FIG. 3A shows the number of unique reads per barcode is presented for a sample of 50 mES cells and 50 mEF cells after ChIP-Seq with H3K4me3. Lighter shades indicate reads with the same barcode on both sides, while darker shades indicates reads with non-matching barcodes on both sides. FIG. 3B shows representative reads from 8 different mES cells and the aggregated data of 50 mESs at the top. FIG. 3C is a correlation matrix between genomic bins of 114 cells (50 mES, 64 mEF). The mES were the first 50 vectors while mEF were last 64, and their separation into two blocks of correlation was observed. After just 3 iterations, an unsupervised algorithm based on the correlations between each cell and two aggregates of cells could separate the two populations, as is shown in FIG. 3D.

Example 4

Figure 8A:
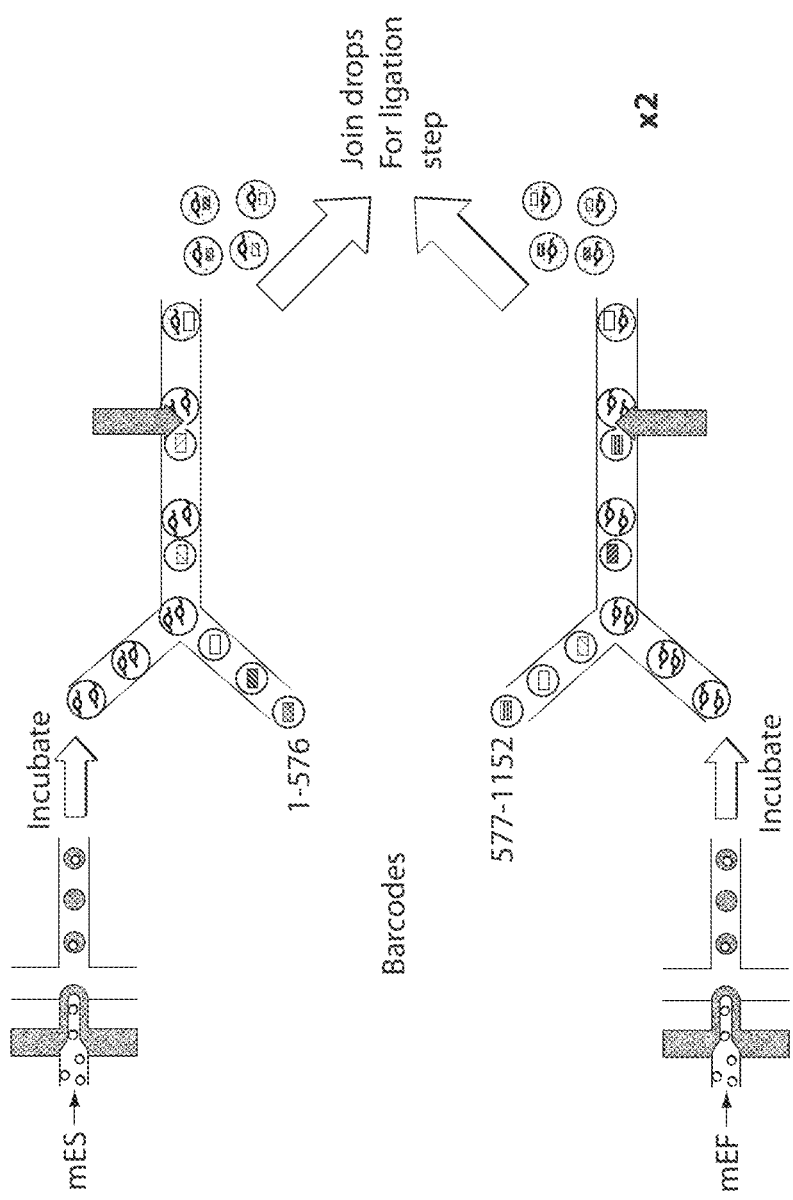
FIGS. 8A-8C illustrate the study of different populations of cells, in yet another embodiment of the invention.

In this example, mouse embryonic stem cells (mES) were compared with mouse embryonic fibroblasts (mEF), using an embodiment of the invention. As shown in FIG. 8A, mESs were encoded with identification sequences 1-576 ("barcodes") while mEFs were encoded with identification sequences 577-1152. (See previous examples for how cells can be encapsulated in droplets with adapters containing suitable identification sequences). In these experiments, the identification sequences were arbitrarily chosen and numbered 1-1152. After ligation, the populations of droplets were combined together.

Figure 8B:
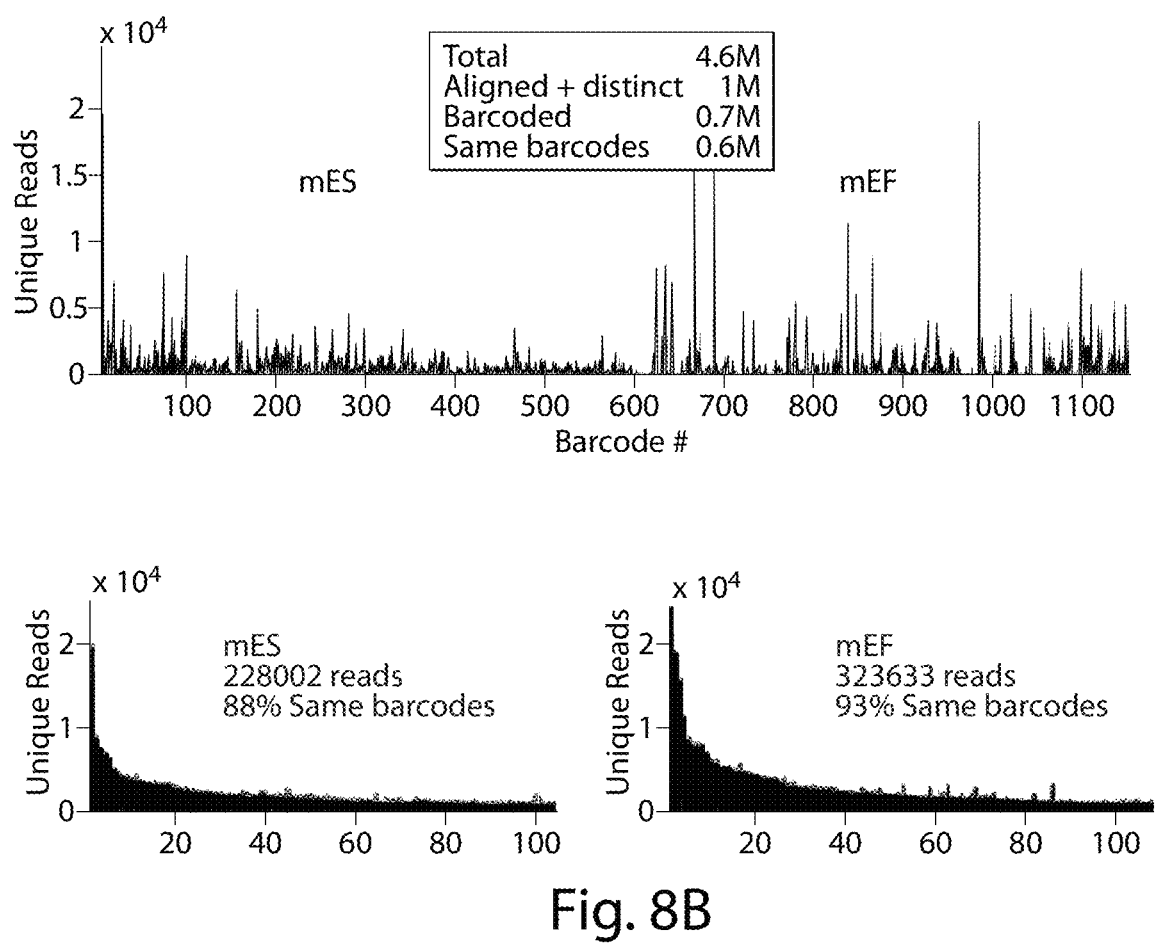
Figure 8C:
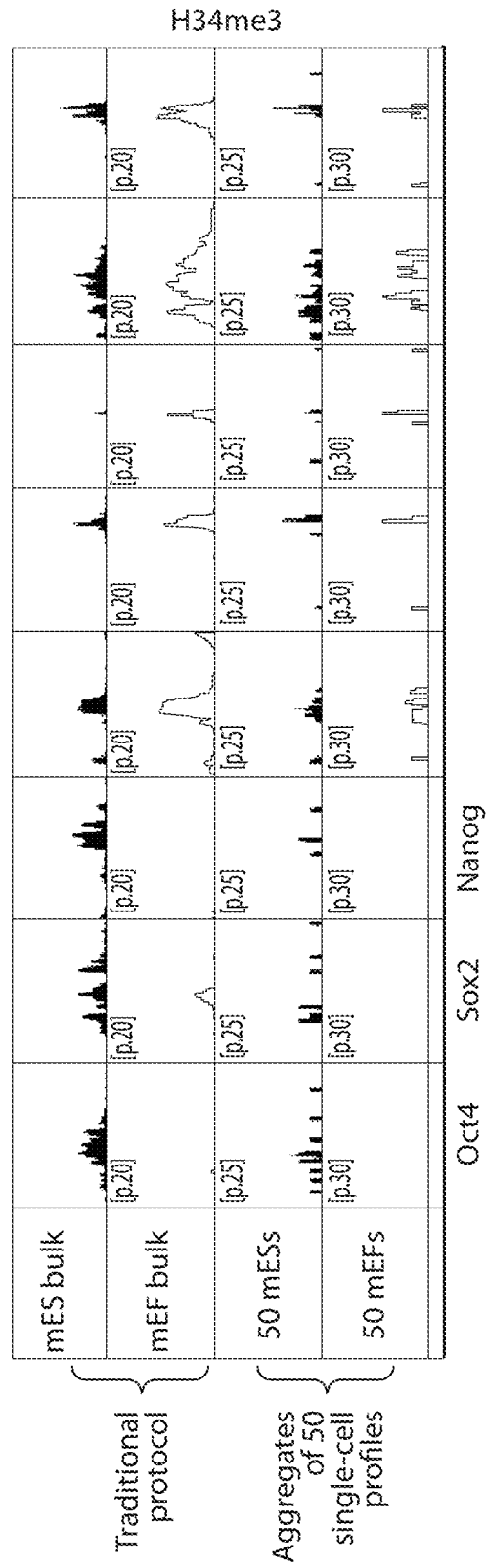

The droplets were then analyzed using ChIP-sequencing, as is shown in FIG. 8B. The H3K4me3 histone was studied in this example. 4.6 million cells were studied, with 1 million distinct reads after alignment and filtering. It was found that each of the relevant barcodes typically tagged 2,000-5,000 distinct DNA fragments from a single cell, representing a sparse binary vector spanning the mouse genome. Of these, about 70% contained adapters on both ends of the DNA. About 10-20% included "cross talk," i.e., the DNA was incorrectly labeled. For each barcode, there were about 3,000-10,000 cells or "reads" that were identified. In addition, the separate reads could be pooled together to restore the epigenomic profile that was measured in a population of cells using more conventional techniques, as is shown in FIG. 8C, where aggregates of 50 single-cell profiles for both mESs and mEFs were compared to traditional protocols for detecting histones.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method comprising:
providing a plurality of cells individually compartmentalized in microfluidic droplets, wherein an individually compartmentalized cell is contained in a first microfluidic droplet, an adapter contained in a second microfluidic droplet,
coalescing the first and the second microfluidic droplet, wherein at least some of the nucleic acid sequences originating from an individually compartmentalized cell become attached to an adapter, the adapter comprising an identification sequence, wherein at least some of the nucleic acid sequences originating from the same cell contain identical identification sequences, and at least some of the nucleic acid sequences originating from different cells contain different identification sequences; and
amplifying at least some of the nucleic acid sequences.

2. The method of claim 1, wherein the adapter comprises a restriction site.

3. The method of claim 1, comprising cleaving the adapter at the restriction site.

4. The method of claim 1, wherein the adapter comprises a primer site.

5. The method of claim 4, wherein the primer site comprises a poly-T primer site or a universal primer site or both.

6. The method of claim 1, wherein the primer site comprises a random primer site.

7. The method of claim 1, wherein the primer site comprises a PCR primer site.

8. The method of claim 1, wherein the identification sequences comprise 8 nucleotides.

9. The method of claim 1, wherein a plurality of adapters are used, comprising a plurality of different identification sequences each having the same length, and a substantially identical restriction site.

10. The method of claim 1, wherein at least some of the cells are prepared from a tissue.

11. The method of claim 1, wherein the adapter is palindromic.

12. The method of claim 1, wherein the plurality of nucleic acid sequences comprise RNA which RNA molecules originate from an individually compartmentalized cell are barcoded or ligated with an identification sequence using the adapter.

13. The method of claim 12, wherein the adapter is coupled to the RNA molecules by direct ligation or by poly-T or random primer-based reverse transcription.

14. The method of claim 1, wherein the adapter is present on a solid support.

* * * * *

SEQUENCE LISTING

```
<160> NUMBER OF SEQ ID NOS: 8

<210> SEQ ID NO 1
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 1
ttaagggctt tcgtatccgg gggaccttaa ttaaggtggg ggggatacct ttcgggttaa      60

<210> SEQ ID NO 2
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 2
taaggtgggg gggatac                                                     17

<210> SEQ ID NO 3
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 3
acacgcagta tcccttcg                                                    18
```

```
<210> SEQ ID NO 4
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 4
actgcgtgta tccgactc                                                    18

<210> SEQ ID NO 5
<211> LENGTH: 46
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (3)..(8)
<223> OTHER INFORMATION: n is a, c, g, or t
<220> FEATURE:
<221> NAME/KEY: misc_feature
<222> LOCATION: (39)..(46)
<223> OTHER INFORMATION: n is a, c, g, or t

<400> SEQUENCE: 5
ncnnnnnngt atcctcagca cccgggtatg tcggatacnn nnnnnn                     46

<210> SEQ ID NO 6
<211> LENGTH: 46
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(8)
<223> OTHER INFORMATION: n is a, c, g, or t
<220> FEATURE:
<221> NAME/KEY: misc_feature
<222> LOCATION: (39)..(44)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t

<400> SEQUENCE: 6
nnnnnnnnca taggagtcgt gggcccatac agcctatgnn nnnngn                     46

<210> SEQ ID NO 7
<211> LENGTH: 46
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (3)..(8)
<223> OTHER INFORMATION: n is a, c, g, or t
<220> FEATURE:
<221> NAME/KEY: misc_feature
<222> LOCATION: (39)..(46)
<223> OTHER INFORMATION: n is a, c, g, or t
```

```
<400> SEQUENCE: 7
ncnnnnnngt atcctcagca cccgggtatg tcggatacnn nnnnnn                46

<210> SEQ ID NO 8
<211> LENGTH: 46
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(8)
<223> OTHER INFORMATION: n is a, c, g, or t
<220> FEATURE:
<221> NAME/KEY: misc_feature
<222> LOCATION: (39)..(44)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t

<400> SEQUENCE: 8
nnnnnnnnca taggagtcgt gggcccatac agcctatgnn nnnngn                 46
```